(12) United States Patent
Minomi et al.

(10) Patent No.: US 10,023,597 B2
(45) Date of Patent: Jul. 17, 2018

(54) RNA INTERFERENCE AGENTS FOR P21 GENE MODULATION

(71) Applicant: Nitto Denko Corporation, Osaka (JP)

(72) Inventors: Kenjirou Minomi, Osaka (JP); Jens Harborth, Carlsbad, CA (US); Cima Cina, San Diego, CA (US); Kwok Yin Tsang, Irvine, CA (US); Wenbin Ying, San Diego, CA (US); Hirokazu Takahashi, Osaka (JP)

(73) Assignee: Nitto Denko Corporation, Osaka (JP)

( * ) Notice: Subject to any disclaimer, the term of this patent is extended or adjusted under 35 U.S.C. 154(b) by 0 days.

(21) Appl. No.: 15/634,771

(22) Filed: Jun. 27, 2017

(65) Prior Publication Data

US 2017/0298086 A1 Oct. 19, 2017

Related U.S. Application Data

(62) Division of application No. 14/979,571, filed on Dec. 28, 2015, now Pat. No. 9,695,206.

(60) Provisional application No. 62/266,668, filed on Dec. 13, 2015, provisional application No. 62/184,209, filed on Jun. 24, 2015.

(30) Foreign Application Priority Data

Dec. 26, 2014 (JP) .................. 2014-266198

(51) Int. Cl.
| | |
|---|---|
| C12N 15/11 | (2006.01) |
| C07F 9/6533 | (2006.01) |
| C12N 15/113 | (2010.01) |
| G01N 33/58 | (2006.01) |
| C12Q 1/02 | (2006.01) |

(52) U.S. Cl.
CPC .......... C07F 9/6533 (2013.01); C12N 15/113 (2013.01); C12N 15/1137 (2013.01); C12Q 1/02 (2013.01); G01N 33/582 (2013.01); C12N 2310/14 (2013.01); C12N 2310/322 (2013.01); C12N 2310/344 (2013.01); C12N 2310/3515 (2013.01); C12N 2310/531 (2013.01); C12N 2320/30 (2013.01)

(58) Field of Classification Search
None
See application file for complete search history.

(56) References Cited

U.S. PATENT DOCUMENTS

| | | | |
|---|---|---|---|
| 8,067,390 B2 | 11/2011 | Merritt |
| 8,367,628 B2 | 2/2013 | Goodwin |
| 8,664,376 B2 | 3/2014 | Niitsu |
| 8,686,052 B2 | 4/2014 | Niitsu |
| 8,710,209 B2 | 4/2014 | Jin |
| 8,741,867 B2 | 6/2014 | Niitsu |
| 8,895,717 B2 | 11/2014 | Sood |
| 9,066,938 B2 | 6/2015 | Saus |
| 9,206,424 B2 | 12/2015 | Jin |
| 2003/0144236 A1 | 7/2003 | Weiss |
| 2003/0165843 A1 | 9/2003 | Shoshan |
| 2005/0142596 A1 | 6/2005 | Krolewski |
| 2005/0233998 A1 | 10/2005 | Jadhav |
| 2005/0245475 A1 | 11/2005 | Khvorova |
| 2007/0031844 A1 | 2/2007 | Khvorova |
| 2007/0083334 A1 | 4/2007 | Mintz |
| 2009/0181379 A1 | 7/2009 | Corrales Izquierdo |
| 2009/0220956 A1 | 9/2009 | Nuyten |
| 2010/0196482 A1 | 8/2010 | Radovic-Moreno |
| 2011/0269819 A1 | 11/2011 | Jones |
| 2012/0142754 A1 | 6/2012 | Niitsu |
| 2013/0004494 A1 | 1/2013 | Heber-Katz |
| 2013/0196434 A1 | 8/2013 | Maier |
| 2013/0330401 A1 | 12/2013 | Payne |
| 2013/0345286 A1 | 12/2013 | Gollob |
| 2014/0005134 A1 | 1/2014 | Saus |
| 2014/0017780 A1 | 1/2014 | Bentwich |
| 2014/0315976 A1 | 10/2014 | Brahmbhatt |
| 2014/0356413 A1 | 12/2014 | Niitsu |

FOREIGN PATENT DOCUMENTS

| | | |
|---|---|---|
| CN | 103695421 A | 4/2014 |
| WO | 2009033284 A1 | 3/2009 |
| WO | 2012170952 A2 | 12/2012 |
| WO | 2013192364 A1 | 12/2013 |
| WO | 2014022739 A2 | 2/2014 |
| WO | 2014136086 A1 | 9/2014 |

OTHER PUBLICATIONS

Ashley, Delivery of Small Interfering RNA by Peptide-Targeted Mesoporous Silica Nanoparticle-Supported Lipid Bilayers, ACS Nano. Author Manuscript. Mar. 27, 2012, vol. 6, pp. 1-28.
Yoshimoto, Obesity-Induced Gut Microbial Metabolite Promotes Liver Cancer Through Senescence Secretome, Nature, 2013, pp. 1-7.
Krizhanovsky, Senescence of Activated Stellate Cells Limits Liver Fibrosis, Cell, Aug. 22, 2008, vol. 134, pp. 657-667.
Gupta, Synergistic Tumor Suppression by Combined Inhibition of Telomerase and CDKN1A6, PNAS, Jul. 14, 2014, E3062-E3071.
Sato, Resolution of Liver Cirrhosis Using Vitamin A-Coupled Liposomes to Deliver siRNA Against a Collagen-Specific Chaperone, Nature Biotechnology, Apr. 2008, vol. 26, pp. 431-442.
Cho, Pirfenidone: An Anti-Fibrotic and Cytoprotective Agent as Therapy for Progressive Kidney Disease, Expert Opin Investig Drugs, Author Manuscript, Mar. 16, 2011, vol. 19, pp. 1-13.

(Continued)

*Primary Examiner* — Ekaterina Poliakova-Georgantas
(74) *Attorney, Agent, or Firm* — Eckman Law Group

(57) ABSTRACT

This invention provides compounds, compositions and methods for modulating the expression of human p21 using RNA interference. The RNA interference molecules can be used in methods for preventing or treating diseases such as malignant tumor. Provided are a range of siRNA structures, having one or more nucleotides being modified or chemically-modified. Advantageous structures include siRNAs with 2'-deoxy nucleotides located in the seed region, as well as other nucleotide modifications.

9 Claims, No Drawings

(56) References Cited

OTHER PUBLICATIONS

Love, Lipid-like materials for low-dose, in vivo gene silencing, Proc Natl Acad Sci U S A., 2010, vol. 107(5), pp. 1864-1869.

Xue, Small RNA combination therapy for lung cancer, Proc Natl Acad Sci U S A, 2014, vol. 111(34), pp. E3553-E3561.

Xu, Enhancing tumor cell response to chemotherapy through nanoparticle-mediated codelivery of siRNA and cisplatin prodrug, Proc Natl Acad Sci U S A, 2013, vol. 110, No. 46, pp. 18638-18643.

Ui-Tei, Functional dissection of siRNA sequence by systematic DNA substitution: modified siRNA with a DNA seed arm is a powerful tool for mammalian gene silencing with significantly reduced off-target effect, Nucleic Acids Res., 2008, vol. 36(7), pp. 2136-2151.

Niitsu, Serum Glutathione-S-Transferase-rr as a Tumor Marker for Gastrointestinal Malignancies, Cancer, Jan. 15, 1989, vol. 63, pp. 317-323.

Hirata, Significance of Glutathione S-Transferase-Pi as a Tumor Marker in Patients with Oral Cancer, Cancer, Nov. 15, 1992, vol. 70, No. 10, pp. 2381-2387.

Hida, Serum Glutathione S-Transferase-Pi Level as a Tumor Marker for Non-Small Cell Lung Cancer, Cancer, Mar. 1, 1994, vol. 73, No. 5, pp. 1377-1382.

Ban, Transfection of Glutathione S-Transferase (GST)-Pi Antisense Complementary DNA Increases the Sensitivity of a Colon Cancer Cell Line to Adriamycin, Cisplatin, Melphalan, and Etoposide, Cancer Research, Aug. 1, 1996, vol. 56, 3577-3582.

Morgan, Tumor Efficacy and Bone Marrow-sparing Properties of TER286, a Cytotoxin Activated by Glutathione S-Transferase, Cancer Research, Jun. 15, 1998, vol. 58, pp. 2568-2575.

Niitsu, A proof of glutathione S-transferase-pi-related multidrug resistance by transfer of antisense gene to cancer cells and sense gene to bone marrow stem cell, Chemico-Biological Interactions, 1998, vol. 111-112, pp. 325-332.

Miyanishi, Glutathione S-Transferase-pi Overexpression Is Closely Associated With K-ras Mutation During Human Colon Carcinogenesis, Gastroenterology, 2001, vol. 121, pp. 865-874.

Matsunaga, C(H)OP refractory chronic lymphocytic leukemia patients in whom salvage chemotherapy chosen by evaluating multiple chemotherapeutic drug-resistant factors was remarkably effective, Int J Clin Oncol, 2003, vol. 8, pp. 326-331.

Hayashi, Suppressive effect of sulindac on branch duct-intraductal papillary mucinous neoplasms, J Gastroenterol, 2009, vol. 44, pp. 964-975.

Morse, The role of glutathione S-transferase P1-1 in colorectal cancer: friend or foe?, Gastroenterology, 2001, vol. 121(4), pp. 1010-1013.

Steckel, Determination of synthetic lethal interactions in KRAS oncogene-dependent cancer cells reveals novel therapeutic targeting strategies, Cell Res., 2012, vol. 22(8), pp. 1227-1245.

Collins, Kras as a key oncogene and therapeutic target in pancreatic cancer, Front Physiol., 2013, vol. 4, Article 107, pp. 1-8.

Elbashir, Functional anatomy of siRNAs for mediating efficient RNAi in *Drosophila melanogaster* embryo lysate, EMBO Journal, 2001, vol. 20, pp. 6877-6888.

Vaishnaw, Review a status report on RNAi therapeutics, Silence, Dec. 31, 2010, vol. 1, pp. 14-26.

Hokaiwado, Glutathione S-transferase Pi mediates proliferation of androgen-independent prostate cancer cells, Carcinogenesis, Jun. 1, 2008, vol. 29, pp. 1134-1138.

Sawers, Glutathione S-transferase P1 (GSTP1) directly influences platinum drug chemosensitivity in ovarian tumour cell lines, British Journal of Cancer, Sep. 9, 2014, vol. 111, pp. 1150-1158.

Tsao et al., Adenovirus-mediated p21 (WAF1 /SDI I/CIP1) gene transfer induces apoptosis of human cervical cancer cell lines, 1999, Journal of Virology, vol. 73, pp. 4983-4990.

Wu et al., Transcriptional regulation during p21 WAF1/CIP-induced apoptosis in human ovarian cancer cells, 2002, JBC, vol. 277, pp. 36329-36337.

Fan et al., An antisense oligodeoxynucleotide to p21 Waf1 /Cip1 causes apoptosis in human breast cancer cells, 2003, Molecular Cancer Therapeutics, vol. 2, pp. 773-782.

Zhang et al., Up-regulation of p21WAF1/CIP1 by small activating RNA inhibits the in vitro and in vivo growth of pancreatic cancer cells, 2012, Tumori, vol. 98, pp. 804-811.

SEQUENCE LISTING

```
<160> NUMBER OF SEQ ID NOS: 86

<210> SEQ ID NO 1
<211> LENGTH: 21
<212> TYPE: RNA
<213> ORGANISM: Artificial Sequence
<220> FEATURE:
<223> OTHER INFORMATION: Description of Artificial Sequence: Synthetic
      oligonucleotide
<220> FEATURE:
<221> NAME/KEY: modified_base
<222> LOCATION: (20)..(21)
<223> OTHER INFORMATION: 2'-methoxy-nucleotide

<400> SEQUENCE: 1
cuuagugacu uuacuuguau u                                                 21

<210> SEQ ID NO 2
<211> LENGTH: 21
<212> TYPE: RNA
<213> ORGANISM: Artificial Sequence
<220> FEATURE:
<223> OTHER INFORMATION: Description of Artificial Sequence: Synthetic
      oligonucleotide
<220> FEATURE:
<221> NAME/KEY: modified_base
<222> LOCATION: (20)..(21)
<223> OTHER INFORMATION: 2'-methoxy-nucleotide
```

-continued

```
<400> SEQUENCE: 2
cagaccagca ugacagauuu u                                              21

<210> SEQ ID NO 3
<211> LENGTH: 21
<212> TYPE: RNA
<213> ORGANISM: Artificial Sequence
<220> FEATURE:
<223> OTHER INFORMATION: Description of Artificial Sequence: Synthetic
      oligonucleotide
<220> FEATURE:
<221> NAME/KEY: modified_base
<222> LOCATION: (20)..(21)
<223> OTHER INFORMATION: 2'-methoxy-nucleotide

<400> SEQUENCE: 3
ugaucuucuc caagaggaau u                                              21

<210> SEQ ID NO 4
<211> LENGTH: 21
<212> TYPE: RNA
<213> ORGANISM: Artificial Sequence
<220> FEATURE:
<223> OTHER INFORMATION: Description of Artificial Sequence: Synthetic
      oligonucleotide
<220> FEATURE:
<221> NAME/KEY: modified_base
<222> LOCATION: (20)..(21)
<223> OTHER INFORMATION: 2'-methoxy-nucleotide

<400> SEQUENCE: 4
guucauugca cuuugauuau u                                              21

<210> SEQ ID NO 5
<211> LENGTH: 21
<212> TYPE: RNA
<213> ORGANISM: Artificial Sequence
<220> FEATURE:
<223> OTHER INFORMATION: Description of Artificial Sequence: Synthetic
      oligonucleotide
<220> FEATURE:
<221> NAME/KEY: modified_base
<222> LOCATION: (20)..(21)
<223> OTHER INFORMATION: 2'-methoxy-nucleotide

<400> SEQUENCE: 5
cauugcacuu ugauuagcau u                                              21

<210> SEQ ID NO 6
<211> LENGTH: 21
<212> TYPE: RNA
<213> ORGANISM: Artificial Sequence
<220> FEATURE:
<223> OTHER INFORMATION: Description of Artificial Sequence: Synthetic
      oligonucleotide
<220> FEATURE:
<221> NAME/KEY: modified_base
<222> LOCATION: (20)..(21)
<223> OTHER INFORMATION: 2'-methoxy-nucleotide

<400> SEQUENCE: 6
agcgauggaa cuucgacuuu u                                              21

<210> SEQ ID NO 7
<211> LENGTH: 21
<212> TYPE: RNA
<213> ORGANISM: Artificial Sequence
<220> FEATURE:
<223> OTHER INFORMATION: Description of Artificial Sequence: Synthetic
```

```
        oligonucleotide
<220> FEATURE:
<221> NAME/KEY: modified_base
<222> LOCATION: (20)..(21)
<223> OTHER INFORMATION: 2'-methoxy-nucleotide

<400> SEQUENCE: 7
gcgauggaac uucgacuuuu u                                        21

<210> SEQ ID NO 8
<211> LENGTH: 21
<212> TYPE: RNA
<213> ORGANISM: Artificial Sequence
<220> FEATURE:
<223> OTHER INFORMATION: Description of Artificial Sequence: Synthetic
      oligonucleotide
<220> FEATURE:
<221> NAME/KEY: modified_base
<222> LOCATION: (20)..(21)
<223> OTHER INFORMATION: 2'-methoxy-nucleotide

<400> SEQUENCE: 8
gggaagggac acacaagaau u                                        21

<210> SEQ ID NO 9
<211> LENGTH: 21
<212> TYPE: RNA
<213> ORGANISM: Artificial Sequence
<220> FEATURE:
<223> OTHER INFORMATION: Description of Artificial Sequence: Synthetic
      oligonucleotide
<220> FEATURE:
<221> NAME/KEY: modified_base
<222> LOCATION: (20)..(21)
<223> OTHER INFORMATION: 2'-methoxy-nucleotide

<400> SEQUENCE: 9
ucuaccucag gcagcucaau u                                        21

<210> SEQ ID NO 10
<211> LENGTH: 21
<212> TYPE: RNA
<213> ORGANISM: Artificial Sequence
<220> FEATURE:
<223> OTHER INFORMATION: Description of Artificial Sequence: Synthetic
      oligonucleotide
<220> FEATURE:
<221> NAME/KEY: modified_base
<222> LOCATION: (20)..(21)
<223> OTHER INFORMATION: 2'-methoxy-nucleotide

<400> SEQUENCE: 10
ggugcucaau aaaugauucu u                                        21

<210> SEQ ID NO 11
<211> LENGTH: 21
<212> TYPE: RNA
<213> ORGANISM: Artificial Sequence
<220> FEATURE:
<223> OTHER INFORMATION: Description of Artificial Sequence: Synthetic
      oligonucleotide
<220> FEATURE:
<221> NAME/KEY: modified_base
<222> LOCATION: (20)..(21)
<223> OTHER INFORMATION: 2'-methoxy-nucleotide

<400> SEQUENCE: 11
caucaucaaa aacuuuggau u                                        21
```

-continued

```
<210> SEQ ID NO 12
<211> LENGTH: 21
<212> TYPE: RNA
<213> ORGANISM: Artificial Sequence
<220> FEATURE:
<223> OTHER INFORMATION: Description of Artificial Sequence: Synthetic
      oligonucleotide
<220> FEATURE:
<221> NAME/KEY: modified_base
<222> LOCATION: (20)..(21)
<223> OTHER INFORMATION: 2'-methoxy-nucleotide

<400> SEQUENCE: 12
aaggagucag acauuuuaau u                                           21

<210> SEQ ID NO 13
<211> LENGTH: 21
<212> TYPE: RNA
<213> ORGANISM: Artificial Sequence
<220> FEATURE:
<223> OTHER INFORMATION: Description of Artificial Sequence: Synthetic
      oligonucleotide
<220> FEATURE:
<221> NAME/KEY: modified_base
<222> LOCATION: (20)..(21)
<223> OTHER INFORMATION: 2'-methoxy-nucleotide

<400> SEQUENCE: 13
gugcugggca uuuuuauuuu u                                           21

<210> SEQ ID NO 14
<211> LENGTH: 21
<212> TYPE: RNA
<213> ORGANISM: Artificial Sequence
<220> FEATURE:
<223> OTHER INFORMATION: Description of Artificial Sequence: Synthetic
      oligonucleotide
<220> FEATURE:
<221> NAME/KEY: modified_base
<222> LOCATION: (20)..(21)
<223> OTHER INFORMATION: 2'-methoxy-nucleotide

<400> SEQUENCE: 14
gccggcuuca ugccagcuau u                                           21

<210> SEQ ID NO 15
<211> LENGTH: 21
<212> TYPE: RNA
<213> ORGANISM: Artificial Sequence
<220> FEATURE:
<223> OTHER INFORMATION: Description of Artificial Sequence: Synthetic
      oligonucleotide
<220> FEATURE:
<221> NAME/KEY: modified_base
<222> LOCATION: (20)..(21)
<223> OTHER INFORMATION: 2'-methoxy-nucleotide

<400> SEQUENCE: 15
gggcaucauc aaaaacuuuu u                                           21

<210> SEQ ID NO 16
<211> LENGTH: 21
<212> TYPE: RNA
<213> ORGANISM: Artificial Sequence
<220> FEATURE:
<223> OTHER INFORMATION: Description of Artificial Sequence: Synthetic
      oligonucleotide
<220> FEATURE:
<221> NAME/KEY: modified_base
<222> LOCATION: (20)..(21)
<223> OTHER INFORMATION: 2'-methoxy-nucleotide
```

<400> SEQUENCE: 16
gaagggcacc cuaguucuau u                                              21

<210> SEQ ID NO 17
<211> LENGTH: 21
<212> TYPE: RNA
<213> ORGANISM: Artificial Sequence
<220> FEATURE:
<223> OTHER INFORMATION: Description of Artificial Sequence: Synthetic
      oligonucleotide
<220> FEATURE:
<221> NAME/KEY: modified_base
<222> LOCATION: (20)..(21)
<223> OTHER INFORMATION: 2'-methoxy-nucleotide

<400> SEQUENCE: 17
caguucauug cacuuugauu u                                              21

<210> SEQ ID NO 18
<211> LENGTH: 21
<212> TYPE: RNA
<213> ORGANISM: Artificial Sequence
<220> FEATURE:
<223> OTHER INFORMATION: Description of Artificial Sequence: Synthetic
      oligonucleotide
<220> FEATURE:
<221> NAME/KEY: modified_base
<222> LOCATION: (20)..(21)
<223> OTHER INFORMATION: 2'-methoxy-nucleotide

<400> SEQUENCE: 18
acaaggaguc agacauuuuu u                                              21

<210> SEQ ID NO 19
<211> LENGTH: 21
<212> TYPE: RNA
<213> ORGANISM: Artificial Sequence
<220> FEATURE:
<223> OTHER INFORMATION: Description of Artificial Sequence: Synthetic
      oligonucleotide
<220> FEATURE:
<221> NAME/KEY: modified_base
<222> LOCATION: (20)..(21)
<223> OTHER INFORMATION: 2'-methoxy-nucleotide

<400> SEQUENCE: 19
uggaggcacu gaagugcuuu u                                              21

<210> SEQ ID NO 20
<211> LENGTH: 21
<212> TYPE: RNA
<213> ORGANISM: Artificial Sequence
<220> FEATURE:
<223> OTHER INFORMATION: Description of Artificial Sequence: Synthetic
      oligonucleotide
<220> FEATURE:
<221> NAME/KEY: modified_base
<222> LOCATION: (20)..(21)
<223> OTHER INFORMATION: 2'-methoxy-nucleotide

<400> SEQUENCE: 20
gcagggacca cacccuguau u                                              21

<210> SEQ ID NO 21
<211> LENGTH: 21
<212> TYPE: RNA
<213> ORGANISM: Artificial Sequence
<220> FEATURE:

<223> OTHER INFORMATION: Description of Artificial Sequence: Synthetic
      oligonucleotide
<220> FEATURE:
<221> NAME/KEY: modified_base
<222> LOCATION: (20)..(21)
<223> OTHER INFORMATION: 2'-methoxy-nucleotide

<400> SEQUENCE: 21 cguacuguu cugugucuuu u                                              21

<210> SEQ ID NO 22
<211> LENGTH: 21
<212> TYPE: RNA
<213> ORGANISM: Artificial Sequence
<220> FEATURE:
<223> OTHER INFORMATION: Description of Artificial Sequence: Synthetic
      oligonucleotide
<220> FEATURE:
<221> NAME/KEY: modified_base
<222> LOCATION: (20)..(21)
<223> OTHER INFORMATION: 2'-methoxy-nucleotide

<400> SEQUENCE: 22
uuaaacaccu ccucauguau u                                             21

<210> SEQ ID NO 23
<211> LENGTH: 21
<212> TYPE: RNA
<213> ORGANISM: Artificial Sequence
<220> FEATURE:
<223> OTHER INFORMATION: Description of Artificial Sequence: Synthetic
      oligonucleotide
<220> FEATURE:
<221> NAME/KEY: modified_base
<222> LOCATION: (20)..(21)
<223> OTHER INFORMATION: 2'-methoxy-nucleotide

<400> SEQUENCE: 23
agacucucag ggucgaaaau u                                             21

<210> SEQ ID NO 24
<211> LENGTH: 21
<212> TYPE: RNA
<213> ORGANISM: Artificial Sequence
<220> FEATURE:
<223> OTHER INFORMATION: Description of Artificial Sequence: Synthetic
      oligonucleotide
<220> FEATURE:
<221> NAME/KEY: modified_base
<222> LOCATION: (20)..(21)
<223> OTHER INFORMATION: 2'-methoxy-nucleotide

<400> SEQUENCE: 24
caugacagau uucuaccacu u                                             21

<210> SEQ ID NO 25
<211> LENGTH: 21
<212> TYPE: RNA
<213> ORGANISM: Artificial Sequence
<220> FEATURE:
<223> OTHER INFORMATION: Description of Artificial Sequence: Synthetic
      oligonucleotide
<220> FEATURE:
<221> NAME/KEY: modified_base
<222> LOCATION: (20)..(21)
<223> OTHER INFORMATION: 2'-methoxy-nucleotide

<400> SEQUENCE: 25
agauuucuac cacuccaaau u                                             21

<210> SEQ ID NO 26
<211> LENGTH: 21
<212> TYPE: RNA
<213> ORGANISM: Artificial Sequence
<220> FEATURE:
<223> OTHER INFORMATION: Description of Artificial Sequence: Synthetic oligonucleotide
<220> FEATURE:
<221> NAME/KEY: modified_base
<222> LOCATION: (20)..(21)
<223> OTHER INFORMATION: 2'-methoxy-nucleotide

<400> SEQUENCE: 26
ccaagaggaa gcccuaaucu u                                              21

<210> SEQ ID NO 27
<211> LENGTH: 21
<212> TYPE: RNA
<213> ORGANISM: Artificial Sequence
<220> FEATURE:
<223> OTHER INFORMATION: Description of Artificial Sequence: Synthetic oligonucleotide
<220> FEATURE:
<221> NAME/KEY: modified_base
<222> LOCATION: (20)..(21)
<223> OTHER INFORMATION: 2'-methoxy-nucleotide

<400> SEQUENCE: 27
gacagcagag gaagaccauu u                                              21

<210> SEQ ID NO 28
<211> LENGTH: 21
<212> TYPE: RNA
<213> ORGANISM: Artificial Sequence
<220> FEATURE:
<223> OTHER INFORMATION: Description of Artificial Sequence: Synthetic oligonucleotide
<220> FEATURE:
<221> NAME/KEY: modified_base
<222> LOCATION: (20)..(21)
<223> OTHER INFORMATION: 2'-methoxy-nucleotide

<400> SEQUENCE: 28
cucccacaau gcugaauauu u                                              21

<210> SEQ ID NO 29
<211> LENGTH: 21
<212> TYPE: RNA
<213> ORGANISM: Artificial Sequence
<220> FEATURE:
<223> OTHER INFORMATION: Description of Artificial Sequence: Synthetic oligonucleotide
<220> FEATURE:
<221> NAME/KEY: modified_base
<222> LOCATION: (20)..(21)
<223> OTHER INFORMATION: 2'-methoxy-nucleotide

<400> SEQUENCE: 29
uacaaguaaa gucacuaagu u                                              21

<210> SEQ ID NO 30
<211> LENGTH: 21
<212> TYPE: RNA
<213> ORGANISM: Artificial Sequence
<220> FEATURE:
<223> OTHER INFORMATION: Description of Artificial Sequence: Synthetic oligonucleotide
<220> FEATURE:
<221> NAME/KEY: modified_base
<222> LOCATION: (20)..(21)

<223> OTHER INFORMATION: 2'-methoxy-nucleotide

<400> SEQUENCE: 30
aaucugucau gcuggucugu u                                              21

<210> SEQ ID NO 31
<211> LENGTH: 21
<212> TYPE: RNA
<213> ORGANISM: Artificial Sequence
<220> FEATURE:
<223> OTHER INFORMATION: Description of Artificial Sequence: Synthetic
      oligonucleotide
<220> FEATURE:
<221> NAME/KEY: modified_base
<222> LOCATION: (20)..(21)
<223> OTHER INFORMATION: 2'-methoxy-nucleotide

<400> SEQUENCE: 31
uuccucuugg agaagaucau u                                              21

<210> SEQ ID NO 32
<211> LENGTH: 21
<212> TYPE: RNA
<213> ORGANISM: Artificial Sequence
<220> FEATURE:
<223> OTHER INFORMATION: Description of Artificial Sequence: Synthetic
      oligonucleotide
<220> FEATURE:
<221> NAME/KEY: modified_base
<222> LOCATION: (20)..(21)
<223> OTHER INFORMATION: 2'-methoxy-nucleotide

<400> SEQUENCE: 32
uaaucaaagu gcaaugaacu u                                              21

<210> SEQ ID NO 33
<211> LENGTH: 21
<212> TYPE: RNA
<213> ORGANISM: Artificial Sequence
<220> FEATURE:
<223> OTHER INFORMATION: Description of Artificial Sequence: Synthetic
      oligonucleotide
<220> FEATURE:
<221> NAME/KEY: modified_base
<222> LOCATION: (20)..(21)
<223> OTHER INFORMATION: 2'-methoxy-nucleotide

<400> SEQUENCE: 33
ugcuaaucaa agugcaaugu u                                              21

<210> SEQ ID NO 34
<211> LENGTH: 21
<212> TYPE: RNA
<213> ORGANISM: Artificial Sequence
<220> FEATURE:
<223> OTHER INFORMATION: Description of Artificial Sequence: Synthetic
      oligonucleotide
<220> FEATURE:
<221> NAME/KEY: modified_base
<222> LOCATION: (20)..(21)
<223> OTHER INFORMATION: 2'-methoxy-nucleotide

<400> SEQUENCE: 34
aagucgaagu uccaucgcuu u                                              21

<210> SEQ ID NO 35
<211> LENGTH: 21
<212> TYPE: RNA
<213> ORGANISM: Artificial Sequence

```
<220> FEATURE:
<223> OTHER INFORMATION: Description of Artificial Sequence: Synthetic
      oligonucleotide
<220> FEATURE:
<221> NAME/KEY: modified_base
<222> LOCATION: (20)..(21)
<223> OTHER INFORMATION: 2'-methoxy-nucleotide

<400> SEQUENCE: 35
aaagucgaag uuccaucgcu u                                              21

<210> SEQ ID NO 36
<211> LENGTH: 21
<212> TYPE: RNA
<213> ORGANISM: Artificial Sequence
<220> FEATURE:
<223> OTHER INFORMATION: Description of Artificial Sequence: Synthetic
      oligonucleotide
<220> FEATURE:
<221> NAME/KEY: modified_base
<222> LOCATION: (20)..(21)
<223> OTHER INFORMATION: 2'-methoxy-nucleotide

<400> SEQUENCE: 36
uucuugugug ucccuucccu u                                              21

<210> SEQ ID NO 37
<211> LENGTH: 21
<212> TYPE: RNA
<213> ORGANISM: Artificial Sequence
<220> FEATURE:
<223> OTHER INFORMATION: Description of Artificial Sequence: Synthetic
      oligonucleotide
<220> FEATURE:
<221> NAME/KEY: modified_base
<222> LOCATION: (20)..(21)
<223> OTHER INFORMATION: 2'-methoxy-nucleotide

<400> SEQUENCE: 37
uugagcugcc ugagguagau u                                              21

<210> SEQ ID NO 38
<211> LENGTH: 21
<212> TYPE: RNA
<213> ORGANISM: Artificial Sequence
<220> FEATURE:
<223> OTHER INFORMATION: Description of Artificial Sequence: Synthetic
      oligonucleotide
<220> FEATURE:
<221> NAME/KEY: modified_base
<222> LOCATION: (20)..(21)
<223> OTHER INFORMATION: 2'-methoxy-nucleotide

<400> SEQUENCE: 38
gaaucauuua uugagcaccu u                                              21

<210> SEQ ID NO 39
<211> LENGTH: 21
<212> TYPE: RNA
<213> ORGANISM: Artificial Sequence
<220> FEATURE:
<223> OTHER INFORMATION: Description of Artificial Sequence: Synthetic
      oligonucleotide
<220> FEATURE:
<221> NAME/KEY: modified_base
<222> LOCATION: (20)..(21)
<223> OTHER INFORMATION: 2'-methoxy-nucleotide

<400> SEQUENCE: 39
uccaaaguuu uugaugaugu u                                              21
```

<210> SEQ ID NO 40
<211> LENGTH: 21
<212> TYPE: RNA
<213> ORGANISM: Artificial Sequence
<220> FEATURE:
<223> OTHER INFORMATION: Description of Artificial Sequence: Synthetic
      oligonucleotide
<220> FEATURE:
<221> NAME/KEY: modified_base
<222> LOCATION: (20)..(21)
<223> OTHER INFORMATION: 2'-methoxy-nucleotide

<400> SEQUENCE: 40
uuaaaauguc ugacuccuuu u                                              21

<210> SEQ ID NO 41
<211> LENGTH: 21
<212> TYPE: RNA
<213> ORGANISM: Artificial Sequence
<220> FEATURE:
<223> OTHER INFORMATION: Description of Artificial Sequence: Synthetic
      oligonucleotide
<220> FEATURE:
<221> NAME/KEY: modified_base
<222> LOCATION: (20)..(21)
<223> OTHER INFORMATION: 2'-methoxy-nucleotide

<400> SEQUENCE: 41
aaauaaaaau gcccagcacu u                                              21

<210> SEQ ID NO 42
<211> LENGTH: 21
<212> TYPE: RNA
<213> ORGANISM: Artificial Sequence
<220> FEATURE:
<223> OTHER INFORMATION: Description of Artificial Sequence: Synthetic
      oligonucleotide
<220> FEATURE:
<221> NAME/KEY: modified_base
<222> LOCATION: (20)..(21)
<223> OTHER INFORMATION: 2'-methoxy-nucleotide

<400> SEQUENCE: 42
uagcuggcau gaagccggcu u                                              21

<210> SEQ ID NO 43
<211> LENGTH: 21
<212> TYPE: RNA
<213> ORGANISM: Artificial Sequence
<220> FEATURE:
<223> OTHER INFORMATION: Description of Artificial Sequence: Synthetic
      oligonucleotide
<220> FEATURE:
<221> NAME/KEY: modified_base
<222> LOCATION: (20)..(21)
<223> OTHER INFORMATION: 2'-methoxy-nucleotide

<400> SEQUENCE: 43
aaaguuuuug augaugcccu u                                              21

<210> SEQ ID NO 44
<211> LENGTH: 21
<212> TYPE: RNA
<213> ORGANISM: Artificial Sequence
<220> FEATURE:
<223> OTHER INFORMATION: Description of Artificial Sequence: Synthetic
      oligonucleotide
<220> FEATURE:
<221> NAME/KEY: modified_base

```
<222> LOCATION: (20)..(21)
<223> OTHER INFORMATION: 2'-methoxy-nucleotide

<400> SEQUENCE: 44
uagaacuagg gugcccuucu u                                              21

<210> SEQ ID NO 45
<211> LENGTH: 21
<212> TYPE: RNA
<213> ORGANISM: Artificial Sequence
<220> FEATURE:
<223> OTHER INFORMATION: Description of Artificial Sequence: Synthetic
      oligonucleotide
<220> FEATURE:
<221> NAME/KEY: modified_base
<222> LOCATION: (20)..(21)
<223> OTHER INFORMATION: 2'-methoxy-nucleotide

<400> SEQUENCE: 45
aucaaagugc aaugaacugu u                                              21

<210> SEQ ID NO 46
<211> LENGTH: 21
<212> TYPE: RNA
<213> ORGANISM: Artificial Sequence
<220> FEATURE:
<223> OTHER INFORMATION: Description of Artificial Sequence: Synthetic
      oligonucleotide
<220> FEATURE:
<221> NAME/KEY: modified_base
<222> LOCATION: (20)..(21)
<223> OTHER INFORMATION: 2'-methoxy-nucleotide

<400> SEQUENCE: 46
aaaaugucug acuccuuguu u                                              21

<210> SEQ ID NO 47
<211> LENGTH: 21
<212> TYPE: RNA
<213> ORGANISM: Artificial Sequence
<220> FEATURE:
<223> OTHER INFORMATION: Description of Artificial Sequence: Synthetic
      oligonucleotide
<220> FEATURE:
<221> NAME/KEY: modified_base
<222> LOCATION: (20)..(21)
<223> OTHER INFORMATION: 2'-methoxy-nucleotide

<400> SEQUENCE: 47
aagcacuuca gugccuccau u                                              21

<210> SEQ ID NO 48
<211> LENGTH: 21
<212> TYPE: RNA
<213> ORGANISM: Artificial Sequence
<220> FEATURE:
<223> OTHER INFORMATION: Description of Artificial Sequence: Synthetic
      oligonucleotide
<220> FEATURE:
<221> NAME/KEY: modified_base
<222> LOCATION: (20)..(21)
<223> OTHER INFORMATION: 2'-methoxy-nucleotide

<400> SEQUENCE: 48
uacagggugu ggucccugcu u                                              21

<210> SEQ ID NO 49
<211> LENGTH: 21
<212> TYPE: RNA
```

<213> ORGANISM: Artificial Sequence
<220> FEATURE:
<223> OTHER INFORMATION: Description of Artificial Sequence: Synthetic
      oligonucleotide
<220> FEATURE:
<221> NAME/KEY: modified_base
<222> LOCATION: (20)..(21)
<223> OTHER INFORMATION: 2'-methoxy-nucleotide

<400> SEQUENCE: 49
aagacacaga acaguacagu u                                           21

<210> SEQ ID NO 50
<211> LENGTH: 21
<212> TYPE: RNA
<213> ORGANISM: Artificial Sequence
<220> FEATURE:
<223> OTHER INFORMATION: Description of Artificial Sequence: Synthetic
      oligonucleotide
<220> FEATURE:
<221> NAME/KEY: modified_base
<222> LOCATION: (20)..(21)
<223> OTHER INFORMATION: 2'-methoxy-nucleotide

<400> SEQUENCE: 50
uacaugagga gguguuuaau u                                           21

<210> SEQ ID NO 51
<211> LENGTH: 21
<212> TYPE: RNA
<213> ORGANISM: Artificial Sequence
<220> FEATURE:
<223> OTHER INFORMATION: Description of Artificial Sequence: Synthetic
      oligonucleotide
<220> FEATURE:
<221> NAME/KEY: modified_base
<222> LOCATION: (20)..(21)
<223> OTHER INFORMATION: 2'-methoxy-nucleotide

<400> SEQUENCE: 51
uuuucgaccc ugagagucuu u                                           21

<210> SEQ ID NO 52
<211> LENGTH: 21
<212> TYPE: RNA
<213> ORGANISM: Artificial Sequence
<220> FEATURE:
<223> OTHER INFORMATION: Description of Artificial Sequence: Synthetic
      oligonucleotide
<220> FEATURE:
<221> NAME/KEY: modified_base
<222> LOCATION: (20)..(21)
<223> OTHER INFORMATION: 2'-methoxy-nucleotide

<400> SEQUENCE: 52
gugguagaaa ucugucaugu u                                           21

<210> SEQ ID NO 53
<211> LENGTH: 21
<212> TYPE: RNA
<213> ORGANISM: Artificial Sequence
<220> FEATURE:
<223> OTHER INFORMATION: Description of Artificial Sequence: Synthetic
      oligonucleotide
<220> FEATURE:
<221> NAME/KEY: modified_base
<222> LOCATION: (20)..(21)
<223> OTHER INFORMATION: 2'-methoxy-nucleotide

<400> SEQUENCE: 53
uuuggagugg uagaaaucuu u                                          21

<210> SEQ ID NO 54
<211> LENGTH: 21
<212> TYPE: RNA
<213> ORGANISM: Artificial Sequence
<220> FEATURE:
<223> OTHER INFORMATION: Description of Artificial Sequence: Synthetic
      oligonucleotide
<220> FEATURE:
<221> NAME/KEY: modified_base
<222> LOCATION: (20)..(21)
<223> OTHER INFORMATION: 2'-methoxy-nucleotide

<400> SEQUENCE: 54
gauuagggcu uccucuuggu u                                          21

<210> SEQ ID NO 55
<211> LENGTH: 21
<212> TYPE: RNA
<213> ORGANISM: Artificial Sequence
<220> FEATURE:
<223> OTHER INFORMATION: Description of Artificial Sequence: Synthetic
      oligonucleotide
<220> FEATURE:
<221> NAME/KEY: modified_base
<222> LOCATION: (20)..(21)
<223> OTHER INFORMATION: 2'-methoxy-nucleotide

<400> SEQUENCE: 55
auggucuucc ucugcugucu u                                          21

<210> SEQ ID NO 56
<211> LENGTH: 21
<212> TYPE: RNA
<213> ORGANISM: Artificial Sequence
<220> FEATURE:
<223> OTHER INFORMATION: Description of Artificial Sequence: Synthetic
      oligonucleotide
<220> FEATURE:
<221> NAME/KEY: modified_base
<222> LOCATION: (20)..(21)
<223> OTHER INFORMATION: 2'-methoxy-nucleotide

<400> SEQUENCE: 56
auauucagca uugugggagu u                                          21

<210> SEQ ID NO 57
<211> LENGTH: 21
<212> TYPE: RNA
<213> ORGANISM: Artificial Sequence
<220> FEATURE:
<223> OTHER INFORMATION: Description of Artificial Sequence: Synthetic
      oligonucleotide
<220> FEATURE:
<221> NAME/KEY: modified_base
<222> LOCATION: (20)..(21)
<223> OTHER INFORMATION: a, c, t, g, u, unknown or other

<400> SEQUENCE: 57
aaggagucag acauuuuaan n                                          21

<210> SEQ ID NO 58
<211> LENGTH: 21
<212> TYPE: RNA
<213> ORGANISM: Artificial Sequence
<220> FEATURE:
<223> OTHER INFORMATION: Description of Artificial Sequence: Synthetic
      oligonucleotide
<220> FEATURE:

```
<221> NAME/KEY: modified_base
<222> LOCATION: (1)..(3)
<223> OTHER INFORMATION: 2'-OMe-nucleotide
<220> FEATURE:
<221> NAME/KEY: modified_base
<222> LOCATION: (8)..(8)
<223> OTHER INFORMATION: 2'-OMe-nucleotide
<220> FEATURE:
<221> NAME/KEY: modified_base
<222> LOCATION: (12)..(12)
<223> OTHER INFORMATION: 2'-OMe-nucleotide
<220> FEATURE:
<221> NAME/KEY: modified_base
<222> LOCATION: (17)..(17)
<223> OTHER INFORMATION: 2'-OMe-nucleotide
<220> FEATURE:
<221> NAME/KEY: modified_base
<222> LOCATION: (20)..(21)
<223> OTHER INFORMATION: 2'-OMe-nucleotide

<400> SEQUENCE: 58
aaggagucag acauuuuaau u                                              21

<210> SEQ ID NO 59
<211> LENGTH: 21
<212> TYPE: RNA
<213> ORGANISM: Artificial Sequence
<220> FEATURE:
<223> OTHER INFORMATION: Description of Artificial Sequence: Synthetic
      oligonucleotide
<220> FEATURE:
<221> NAME/KEY: modified_base
<222> LOCATION: (1)..(3)
<223> OTHER INFORMATION: 2'-OMe-nucleotide
<220> FEATURE:
<221> NAME/KEY: modified_base
<222> LOCATION: (8)..(8)
<223> OTHER INFORMATION: 2'-OMe-nucleotide
<220> FEATURE:
<221> NAME/KEY: modified_base
<222> LOCATION: (12)..(12)
<223> OTHER INFORMATION: 2'-OMe-nucleotide
<220> FEATURE:
<221> NAME/KEY: modified_base
<222> LOCATION: (14)..(15)
<223> OTHER INFORMATION: 2'-OMe-nucleotide
<220> FEATURE:
<221> NAME/KEY: modified_base
<222> LOCATION: (17)..(17)
<223> OTHER INFORMATION: 2'-OMe-nucleotide
<220> FEATURE:
<221> NAME/KEY: modified_base
<222> LOCATION: (20)..(21)
<223> OTHER INFORMATION: 2'-OMe-nucleotide

<400> SEQUENCE: 59
aaggagucag acauuuuaau u                                              21

<210> SEQ ID NO 60
<211> LENGTH: 21
<212> TYPE: RNA
<213> ORGANISM: Artificial Sequence
<220> FEATURE:
<223> OTHER INFORMATION: Description of Artificial Sequence: Synthetic
      oligonucleotide
<220> FEATURE:
<221> NAME/KEY: modified_base
<222> LOCATION: (1)..(3)
<223> OTHER INFORMATION: 2'-OMe-nucleotide
<220> FEATURE:
<221> NAME/KEY: modified_base
<222> LOCATION: (8)..(8)
<223> OTHER INFORMATION: 2'-OMe-nucleotide
<220> FEATURE:
<221> NAME/KEY: modified_base
```

-continued

```
<222> LOCATION: (12)..(12)
<223> OTHER INFORMATION: 2'-OMe-nucleotide
<220> FEATURE:
<221> NAME/KEY: modified_base
<222> LOCATION: (14)..(15)
<223> OTHER INFORMATION: 2'-OMe-nucleotide
<220> FEATURE:
<221> NAME/KEY: modified_base
<222> LOCATION: (17)..(17)
<223> OTHER INFORMATION: 2'-OMe-nucleotide
<220> FEATURE:
<221> NAME/KEY: modified_base
<222> LOCATION: (20)..(21)
<223> OTHER INFORMATION: 2'-OMe-nucleotide

<400> SEQUENCE: 60
aaggagucag acauuuuaau u                                          21

<210> SEQ ID NO 61
<211> LENGTH: 21
<212> TYPE: RNA
<213> ORGANISM: Artificial Sequence
<220> FEATURE:
<223> OTHER INFORMATION: Description of Artificial Sequence: Synthetic
      oligonucleotide
<220> FEATURE:
<221> NAME/KEY: modified_base
<222> LOCATION: (1)..(3)
<223> OTHER INFORMATION: 2'-OMe-nucleotide
<220> FEATURE:
<221> NAME/KEY: modified_base
<222> LOCATION: (8)..(8)
<223> OTHER INFORMATION: 2'-OMe-nucleotide
<220> FEATURE:
<221> NAME/KEY: modified_base
<222> LOCATION: (12)..(12)
<223> OTHER INFORMATION: 2'-OMe-nucleotide
<220> FEATURE:
<221> NAME/KEY: modified_base
<222> LOCATION: (17)..(17)
<223> OTHER INFORMATION: 2'-OMe-nucleotide
<220> FEATURE:
<221> NAME/KEY: modified_base
<222> LOCATION: (20)..(21)
<223> OTHER INFORMATION: 2'-OMe-nucleotide

<400> SEQUENCE: 61
aaggagucag acauuuuaau u                                          21

<210> SEQ ID NO 62
<211> LENGTH: 21
<212> TYPE: RNA
<213> ORGANISM: Artificial Sequence
<220> FEATURE:
<223> OTHER INFORMATION: Description of Artificial Sequence: Synthetic
      oligonucleotide
<220> FEATURE:
<221> NAME/KEY: modified_base
<222> LOCATION: (20)..(21)
<223> OTHER INFORMATION: 2'-OMe-nucleotide

<400> SEQUENCE: 62
aaggagucag acauuuuaau u                                          21

<210> SEQ ID NO 63
<211> LENGTH: 21
<212> TYPE: RNA
<213> ORGANISM: Artificial Sequence
<220> FEATURE:
<223> OTHER INFORMATION: Description of Artificial Sequence: Synthetic
      oligonucleotide
<220> FEATURE:
<221> NAME/KEY: modified_base
```

```
<222> LOCATION: (20)..(21)
<223> OTHER INFORMATION: 2'-OMe-nucleotide

<400> SEQUENCE: 63
aaggagucag acauuuuaau u                                              21

<210> SEQ ID NO 64
<211> LENGTH: 21
<212> TYPE: RNA
<213> ORGANISM: Artificial Sequence
<220> FEATURE:
<223> OTHER INFORMATION: Description of Artificial Sequence: Synthetic
      oligonucleotide
<220> FEATURE:
<221> NAME/KEY: modified_base
<222> LOCATION: (20)..(21)
<223> OTHER INFORMATION: 2'-OMe-nucleotide

<400> SEQUENCE: 64
aaggagucag acauuuuaau u                                              21

<210> SEQ ID NO 65
<211> LENGTH: 21
<212> TYPE: RNA
<213> ORGANISM: Artificial Sequence
<220> FEATURE:
<223> OTHER INFORMATION: Description of Artificial Sequence: Synthetic
      oligonucleotide
<220> FEATURE:
<221> NAME/KEY: modified_base
<222> LOCATION: (20)..(21)
<223> OTHER INFORMATION: 2'-OMe-nucleotide

<400> SEQUENCE: 65
aaggagucag acauuuuaau u                                              21

<210> SEQ ID NO 66
<211> LENGTH: 21
<212> TYPE: RNA
<213> ORGANISM: Artificial Sequence
<220> FEATURE:
<223> OTHER INFORMATION: Description of Artificial Sequence: Synthetic
      oligonucleotide
<220> FEATURE:
<221> NAME/KEY: modified_base
<222> LOCATION: (20)..(21)
<223> OTHER INFORMATION: 2'-OMe-nucleotide

<400> SEQUENCE: 66
aaggagucag acauuuuaau u                                              21

<210> SEQ ID NO 67
<211> LENGTH: 21
<212> TYPE: RNA
<213> ORGANISM: Artificial Sequence
<220> FEATURE:
<223> OTHER INFORMATION: Description of Artificial Sequence: Synthetic
      oligonucleotide
<220> FEATURE:
<221> NAME/KEY: modified_base
<222> LOCATION: (20)..(21)
<223> OTHER INFORMATION: 2'-OMe-nucleotide

<400> SEQUENCE: 67
aaggagucag acauuuuaau u                                              21

<210> SEQ ID NO 68
<211> LENGTH: 21
<212> TYPE: RNA
```

```
<213> ORGANISM: Artificial Sequence
<220> FEATURE:
<223> OTHER INFORMATION: Description of Artificial Sequence: Synthetic
      oligonucleotide
<220> FEATURE:
<221> NAME/KEY: modified_base
<222> LOCATION: (8)..(8)
<223> OTHER INFORMATION: 2'-OMe-nucleotide
<220> FEATURE:
<221> NAME/KEY: modified_base
<222> LOCATION: (12)..(12)
<223> OTHER INFORMATION: 2'-OMe-nucleotide
<220> FEATURE:
<221> NAME/KEY: modified_base
<222> LOCATION: (17)..(17)
<223> OTHER INFORMATION: 2'-OMe-nucleotide
<220> FEATURE:
<221> NAME/KEY: modified_base
<222> LOCATION: (20)..(21)
<223> OTHER INFORMATION: 2'-OMe-nucleotide

<400> SEQUENCE: 68
aaggagucag acauuuuaau u                                              21

<210> SEQ ID NO 69
<211> LENGTH: 21
<212> TYPE: RNA
<213> ORGANISM: Artificial Sequence
<220> FEATURE:
<223> OTHER INFORMATION: Description of Artificial Sequence: Synthetic
      oligonucleotide
<220> FEATURE:
<221> NAME/KEY: modified_base
<222> LOCATION: (1)..(3)
<223> OTHER INFORMATION: 2'-OMe-nucleotide
<220> FEATURE:
<221> NAME/KEY: modified_base
<222> LOCATION: (20)..(21)
<223> OTHER INFORMATION: 2'-OMe-nucleotide

<400> SEQUENCE: 69
aaggagucag acauuuuaau u                                              21

<210> SEQ ID NO 70
<211> LENGTH: 21
<212> TYPE: RNA
<213> ORGANISM: Artificial Sequence
<220> FEATURE:
<223> OTHER INFORMATION: Description of Artificial Sequence: Synthetic
      oligonucleotide
<220> FEATURE:
<221> NAME/KEY: modified_base
<222> LOCATION: (1)..(3)
<223> OTHER INFORMATION: 2'-OMe-nucleotide
<220> FEATURE:
<221> NAME/KEY: modified_base
<222> LOCATION: (8)..(8)
<223> OTHER INFORMATION: 2'-OMe-nucleotide
<220> FEATURE:
<221> NAME/KEY: modified_base
<222> LOCATION: (12)..(12)
<223> OTHER INFORMATION: 2'-OMe-nucleotide
<220> FEATURE:
<221> NAME/KEY: modified_base
<222> LOCATION: (17)..(17)
<223> OTHER INFORMATION: 2'-OMe-nucleotide
<220> FEATURE:
<221> NAME/KEY: modified_base
<222> LOCATION: (20)..(21)
<223> OTHER INFORMATION: 2'-OMe-nucleotide

<400> SEQUENCE: 70
aaggagucag acauuuuaau u                                              21
```

<210> SEQ ID NO 71
<211> LENGTH: 21
<212> TYPE: DNA
<213> ORGANISM: Artificial Sequence
<220> FEATURE:
<223> OTHER INFORMATION: Description of Artificial Sequence: Synthetic
      oligonucleotide
<220> FEATURE:
<223> OTHER INFORMATION: Description of Combined DNA/RNA Molecule:
      Synthetic oligonucleotide
<220> FEATURE:
<221> NAME/KEY: modified_base
<222> LOCATION: (20)..(21)
<223> OTHER INFORMATION: a, c, t, g, u, unknown or other

<400> SEQUENCE: 71
uuaaaauguc ugacuccuun n                                           21

<210> SEQ ID NO 72
<211> LENGTH: 21
<212> TYPE: DNA
<213> ORGANISM: Artificial Sequence
<220> FEATURE:
<223> OTHER INFORMATION: Description of Artificial Sequence: Synthetic
      oligonucleotide
<220> FEATURE:
<223> OTHER INFORMATION: Description of Combined DNA/RNA Molecule:
      Synthetic oligonucleotide
<220> FEATURE:
<221> NAME/KEY: modified_base
<222> LOCATION: (2)..(2)
<223> OTHER INFORMATION: 2'-OMe-nucleotide
<220> FEATURE:
<221> NAME/KEY: modified_base
<222> LOCATION: (7)..(7)
<223> OTHER INFORMATION: 2'-OMe-nucleotide
<220> FEATURE:
<221> NAME/KEY: modified_base
<222> LOCATION: (11)..(11)
<223> OTHER INFORMATION: 2'-OMe-nucleotide
<220> FEATURE:
<221> NAME/KEY: modified_base
<222> LOCATION: (20)..(21)
<223> OTHER INFORMATION: 2'-OMe-nucleotide

<400> SEQUENCE: 72
uuaaaauguc ugacuccuuu u                                           21

<210> SEQ ID NO 73
<211> LENGTH: 21
<212> TYPE: DNA
<213> ORGANISM: Artificial Sequence
<220> FEATURE:
<223> OTHER INFORMATION: Description of Artificial Sequence: Synthetic
      oligonucleotide
<220> FEATURE:
<223> OTHER INFORMATION: Description of Combined DNA/RNA Molecule:
      Synthetic oligonucleotide
<220> FEATURE:
<221> NAME/KEY: modified_base
<222> LOCATION: (2)..(2)
<223> OTHER INFORMATION: 2'-OMe-nucleotide
<220> FEATURE:
<221> NAME/KEY: modified_base
<222> LOCATION: (7)..(7)
<223> OTHER INFORMATION: 2'-OMe-nucleotide
<220> FEATURE:
<221> NAME/KEY: modified_base
<222> LOCATION: (11)..(11)
<223> OTHER INFORMATION: 2'-OMe-nucleotide
<220> FEATURE:
<221> NAME/KEY: modified_base
<222> LOCATION: (20)..(21)
<223> OTHER INFORMATION: 2'-OMe-nucleotide

```
<400> SEQUENCE: 73
uuaaaauguc ugacuccuuu u                                              21

<210> SEQ ID NO 74
<211> LENGTH: 21
<212> TYPE: DNA
<213> ORGANISM: Artificial Sequence
<220> FEATURE:
<223> OTHER INFORMATION: Description of Artificial Sequence: Synthetic
      oligonucleotide
<220> FEATURE:
<223> OTHER INFORMATION: Description of Combined DNA/RNA Molecule:
      Synthetic oligonucleotide
<220> FEATURE:
<221> NAME/KEY: modified_base
<222> LOCATION: (2)..(2)
<223> OTHER INFORMATION: 2'-OMe-nucleotide
<220> FEATURE:
<221> NAME/KEY: modified_base
<222> LOCATION: (20)..(21)
<223> OTHER INFORMATION: 2'-OMe-nucleotide

<400> SEQUENCE: 74
uuaaaauguc ugacuccuuu u                                              21

<210> SEQ ID NO 75
<211> LENGTH: 21
<212> TYPE: DNA
<213> ORGANISM: Artificial Sequence
<220> FEATURE:
<223> OTHER INFORMATION: Description of Artificial Sequence: Synthetic
      oligonucleotide
<220> FEATURE:
<223> OTHER INFORMATION: Description of Combined DNA/RNA Molecule:
      Synthetic oligonucleotide
<220> FEATURE:
<221> NAME/KEY: modified_base
<222> LOCATION: (2)..(2)
<223> OTHER INFORMATION: 2'-OMe-nucleotide
<220> FEATURE:
<221> NAME/KEY: modified_base
<222> LOCATION: (20)..(21)
<223> OTHER INFORMATION: 2'-OMe-nucleotide

<400> SEQUENCE: 75
uuaaaauguc ugacuccuuu u                                              21

<210> SEQ ID NO 76
<211> LENGTH: 21
<212> TYPE: DNA
<213> ORGANISM: Artificial Sequence
<220> FEATURE:
<223> OTHER INFORMATION: Description of Artificial Sequence: Synthetic
      oligonucleotide
<220> FEATURE:
<223> OTHER INFORMATION: Description of Combined DNA/RNA Molecule:
      Synthetic oligonucleotide
<220> FEATURE:
<221> NAME/KEY: modified_base
<222> LOCATION: (7)..(7)
<223> OTHER INFORMATION: 2'-deoxy-nucleotide
<220> FEATURE:
<221> NAME/KEY: modified_base
<222> LOCATION: (20)..(21)
<223> OTHER INFORMATION: 2'-OMe-nucleotide

<400> SEQUENCE: 76
uuaaaauguc ugacuccuuu u                                              21

<210> SEQ ID NO 77
```

```
<211> LENGTH: 21
<212> TYPE: DNA
<213> ORGANISM: Artificial Sequence
<220> FEATURE:
<223> OTHER INFORMATION: Description of Artificial Sequence: Synthetic
      oligonucleotide
<220> FEATURE:
<223> OTHER INFORMATION: Description of Combined DNA/RNA Molecule:
      Synthetic oligonucleotide
<220> FEATURE:
<221> NAME/KEY: modified_base
<222> LOCATION: (7)..(7)
<223> OTHER INFORMATION: 2'-deoxy-nucleotide
<220> FEATURE:
<221> NAME/KEY: modified_base
<222> LOCATION: (20)..(21)
<223> OTHER INFORMATION: 2'-OMe-nucleotide

<400> SEQUENCE: 77
uuaaaauguc ugacuccuuu u                                             21

<210> SEQ ID NO 78
<211> LENGTH: 21
<212> TYPE: DNA
<213> ORGANISM: Artificial Sequence
<220> FEATURE:
<223> OTHER INFORMATION: Description of Artificial Sequence: Synthetic
      oligonucleotide
<220> FEATURE:
<223> OTHER INFORMATION: Description of Combined DNA/RNA Molecule:
      Synthetic oligonucleotide
<220> FEATURE:
<221> NAME/KEY: modified_base
<222> LOCATION: (1)..(1)
<223> OTHER INFORMATION: 2'-deoxy-nucleotide
<220> FEATURE:
<221> NAME/KEY: modified_base
<222> LOCATION: (7)..(7)
<223> OTHER INFORMATION: 2'-deoxy-nucleotide
<220> FEATURE:
<221> NAME/KEY: modified_base
<222> LOCATION: (20)..(21)
<223> OTHER INFORMATION: 2'-OMe-nucleotide

<400> SEQUENCE: 78
uuaaaauguc ugacuccuuu u                                             21

<210> SEQ ID NO 79
<211> LENGTH: 21
<212> TYPE: DNA
<213> ORGANISM: Artificial Sequence
<220> FEATURE:
<223> OTHER INFORMATION: Description of Artificial Sequence: Synthetic
      oligonucleotide
<220> FEATURE:
<223> OTHER INFORMATION: Description of Combined DNA/RNA Molecule:
      Synthetic oligonucleotide
<220> FEATURE:
<221> NAME/KEY: modified_base
<222> LOCATION: (7)..(7)
<223> OTHER INFORMATION: 2'-deoxy-nucleotide
<220> FEATURE:
<221> NAME/KEY: modified_base
<222> LOCATION: (20)..(21)
<223> OTHER INFORMATION: 2'-OMe-nucleotide

<400> SEQUENCE: 79
uuaaaauguc ugacuccuuu u                                             21

<210> SEQ ID NO 80
<211> LENGTH: 21
<212> TYPE: DNA
<213> ORGANISM: Artificial Sequence
```

```
<220> FEATURE:
<223> OTHER INFORMATION: Description of Artificial Sequence: Synthetic
      oligonucleotide
<220> FEATURE:
<223> OTHER INFORMATION: Description of Combined DNA/RNA Molecule:
      Synthetic oligonucleotide
<220> FEATURE:
<221> NAME/KEY: modified_base
<222> LOCATION: (20)..(21)
<223> OTHER INFORMATION: 2'-OMe-nucleotide

<400> SEQUENCE: 80
uuaaaauguc ugacuccuuu u                                             21

<210> SEQ ID NO 81
<211> LENGTH: 21
<212> TYPE: RNA
<213> ORGANISM: Artificial Sequence
<220> FEATURE:
<223> OTHER INFORMATION: Description of Artificial Sequence: Synthetic
      oligonucleotide
<220> FEATURE:
<221> NAME/KEY: modified_base
<222> LOCATION: (2)..(2)
<223> OTHER INFORMATION: 2'-OMe-nucleotide
<220> FEATURE:
<221> NAME/KEY: modified_base
<222> LOCATION: (7)..(7)
<223> OTHER INFORMATION: 2'-OMe-nucleotide
<220> FEATURE:
<221> NAME/KEY: modified_base
<222> LOCATION: (11)..(11)
<223> OTHER INFORMATION: 2'-OMe-nucleotide
<220> FEATURE:
<221> NAME/KEY: modified_base
<222> LOCATION: (20)..(21)
<223> OTHER INFORMATION: 2'-OMe-nucleotide

<400> SEQUENCE: 81
uuaaaauguc ugacuccuuu u                                             21

<210> SEQ ID NO 82
<211> LENGTH: 21
<212> TYPE: RNA
<213> ORGANISM: Artificial Sequence
<220> FEATURE:
<223> OTHER INFORMATION: Description of Artificial Sequence: Synthetic
      oligonucleotide
<220> FEATURE:
<221> NAME/KEY: modified_base
<222> LOCATION: (20)..(21)
<223> OTHER INFORMATION: 2'-OMe-nucleotide

<400> SEQUENCE: 82
uuaaaauguc ugacuccuuu u                                             21

<210> SEQ ID NO 83
<211> LENGTH: 21
<212> TYPE: RNA
<213> ORGANISM: Artificial Sequence
<220> FEATURE:
<223> OTHER INFORMATION: Description of Artificial Sequence: Synthetic
      oligonucleotide
<220> FEATURE:
<221> NAME/KEY: modified_base
<222> LOCATION: (20)..(21)
<223> OTHER INFORMATION: 2'-OMe-nucleotide

<400> SEQUENCE: 83
uuaaaauguc ugacuccuuu u                                             21
```

```
<210> SEQ ID NO 84
<211> LENGTH: 21
<212> TYPE: RNA
<213> ORGANISM: Artificial Sequence
<220> FEATURE:
<223> OTHER INFORMATION: Description of Artificial Sequence: Synthetic
      oligonucleotide
<220> FEATURE:
<221> NAME/KEY: modified_base
<222> LOCATION: (20)..(21)
<223> OTHER INFORMATION: 2'-OMe-nucleotide

<400> SEQUENCE: 84
uuaaaauguc ugacuccuuu u                                              21

<210> SEQ ID NO 85
<211> LENGTH: 21
<212> TYPE: DNA
<213> ORGANISM: Artificial Sequence
<220> FEATURE:
<223> OTHER INFORMATION: Description of Artificial Sequence: Synthetic
      oligonucleotide
<220> FEATURE:
<223> OTHER INFORMATION: Description of Combined DNA/RNA Molecule:
      Synthetic oligonucleotide

<400> SEQUENCE: 85
uccuaagagu gcugggcaut t                                              21

<210> SEQ ID NO 86
<211> LENGTH: 21
<212> TYPE: DNA
<213> ORGANISM: Artificial Sequence
<220> FEATURE:
<223> OTHER INFORMATION: Description of Artificial Sequence: Synthetic
      oligonucleotide
<220> FEATURE:
<223> OTHER INFORMATION: Description of Combined DNA/RNA Molecule:
      Synthetic oligonucleotide

<400> SEQUENCE: 86
augcccagca cucuuaggat t                                              21
```

RNA INTERFERENCE AGENTS FOR P21 GENE MODULATION

SEQUENCE LISTING

This application includes a Sequence Listing submitted electronically as an ASCII file created on Dec. 23, 2015, named ND5123591US_SL.txt, which is 31,227 bytes in size, and is hereby incorporated by reference in its entirety.

BACKGROUND OF THE INVENTION p21 is a cell cycle-regulating protein that is encoded by CDKN1A gene and belongs to the CIP/KIP family. This protein has the function of inhibiting cell cycle progression at the G1 phase and the G2/M phase by inhibiting the effect of a cyclin-CDK complex through binding to the complex. Specifically, the p21 gene undergoes activation by p53, one of tumor suppressor genes. It has been reported that upon activation of p53 due to DNA damage or the like, p53 activates p21 so that the cell cycle is arrested at the G1 phase and the G2/M phase.

p21 is overexpressed in a variety of human cancers including prostate, cervical, breast and squamous cell carcinomas and, in many cases, p21 upregulation correlates positively with tumor grade, invasiveness and aggressiveness. See, e.g., Chang et al., Proc. Natl. Acad. Sci. USA, 2000, Vol. 97, No. 8, pp. 4291-96. Also, up-regulation of p21 has been reported to be associated with tumorigenicity and poor prognosis in many forms of cancers, including brain, prostate, ovarian, breast, and esophageal cell cancers. See, e.g., Winters et al., Breast Cancer Research, 2003, Vol. 5, No. 6, pp. R242-R249. Also, the disease can be age related diseases, including atherosclerosis, Alzheimer's disease, amyloidosis, and arthritis. See, e.g., Chang et al., Proc. Natl. Acad. Sci. USA, 2000, Vol. 97, No. 8, pp. 4291-96.

There is an urgent need for compositions and methods for modulating the expression of genes associated with cancer. Therapeutics for inhibition of p21 expression will require highly potent siRNA sequences and structures.

What is needed are siRNA sequences, compounds and structures for modulating p21 expression, with uses for treating disease, such as malignant tumors.

BRIEF SUMMARY

This invention relates to the fields of biopharmaceuticals and therapeutics composed of nucleic acid based molecules. More particularly, this invention relates to compounds and compositions utilizing RNA interference (RNAi) for modulating the expression of human p21.

This invention relates to compounds, compositions and methods for modulating the expression of human p21 using RNA interference.

In some embodiments, this invention provides molecules for RNA interference gene silencing of p21.

In further embodiments, the structures, molecules and compositions of this invention can be used in methods for preventing or treating diseases, or ameliorating symptoms of conditions or disorders associated with p21, including malignant tumor.

Embodiments of this invention include the following:

A nucleic acid molecule for inhibiting expression of p21 comprising a sense strand and an antisense strand, wherein the strands form a duplex region. The nucleic acid molecule can have one or more of the nucleotides in the duplex region being modified or chemically-modified.

In some embodiments, the nucleic acid molecule can have modified or chemically-modified nucleotides are 2'-deoxy nucleotides, 2'-O-alkyl substituted nucleotides, 2'-deoxy-2'-fluoro substituted nucleotides, phosphorothioate nucleotides, locked nucleotides, or any combination thereof.

More particularly, the nucleic acid siRNA molecule may have an antisense strand having deoxynucleotides in a plurality of positions, the plurality of positions being one of the following:

each of positions 4, 6 and 8, from the 5' end of the antisense strand;

each of positions 3, 5 and 7, from the 5' end of the antisense strand;

each of positions 1, 3, 5 and 7, from the 5' end of the antisense strand;

each of positions 3-8, from the 5' end of the antisense strand; or each of positions 5-8, from the 5' end of the antisense strand.

In certain embodiments, the nucleic acid siRNA molecule can have one or more 2'-deoxy-2'-fluoro substituted nucleotides in the duplex region.

This invention further provides nucleic acid molecules which cab inhibit expression of p21 mRNA with an IC50 of less than 50 pM.

In certain embodiments, the nucleic acid siRNA molecules can inhibit expression of p21 mRNA levels by at least 25% in vivo after a single administration of the molecules.

Embodiments of this invention further provide pharmaceutical compositions containing the nucleic acid molecules and a pharmaceutically acceptable carrier. In some embodiments, the carrier can be a lipid molecule or liposome. This invention further provides vectors or cells comprising any of the nucleic acid siRNA molecules.

This invention also contemplates methods for treating a disease by administering to a subject in need a composition containing any of the nucleic acid siRNA molecules. For example, the disease can be malignant tumor, cancer, cancer caused by cells expressing mutated KRAS, sarcoma, or carcinoma, among others.

DETAILED DESCRIPTION OF THE INVENTION

This invention relates to compounds, compositions and methods for nucleic acid based therapeutics for modulating expression of p21.

In some embodiments, this invention provides molecules active in RNA interference, as well as structures and compositions that can silence expression of p21.

The structures and compositions of this disclosure can be used in preventing or treating various diseases such as malignant tumor.

In further embodiments, this invention provides compositions for delivery and uptake of one or more therapeutic RNAi molecules of this invention, as well as methods of use thereof. The RNA-based compositions of this invention can be used in methods for preventing or treating malignant tumors, such as cancers.

Therapeutic compositions of this invention include nucleic acid molecules that are active in RNA interference. The therapeutic nucleic acid molecules can be targeted to CDKN1A (p21) for gene silencing.

In various embodiments, this invention provides a range of molecules that can be active as a small interfering RNA (siRNA), and can regulate or silence p21 expression.

The siRNAs of this invention can be used for preventing or treating malignant tumors.

Embodiments of this invention further provide a vehicle, formulation, or lipid nanoparticle formulation for delivery of the inventive siRNAs to subjects in need of preventing or treating a malignant tumor. This invention further contemplates methods for administering siRNAs as therapeutics to mammals.

The therapeutic molecules and compositions of this invention can be used for RNA interference directed to preventing or treating a p21 associated disease, by administering a compound or composition to a subject in need.

The methods of this invention can utilize the inventive compounds for preventing or treating malignant tumor. The malignant tumor can be presented in various diseases, for example, cancers that highly expressing p21, sarcomas, fibrosarcoma, malignant fibrous histiocytoma, liposarcoma, rhabdomyosarcoma, leiomyosarcoma, angiosarcoma, Kaposi's sarcoma, lymphangiosarcoma, synovial sarcoma, chondrosarcoma, osteosarcoma, carcinomas, brain tumor, head and neck cancer, breast cancer, lung cancer, esophageal cancer, stomach cancer, duodenal cancer, appendix cancer, colorectal cancer, rectal cancer, liver cancer, pancreatic cancer, gallbladder cancer, bile duct cancer, anus cancer, kidney cancer, urethral cancer, urinary bladder cancer, prostate cancer, testicular cancer, uterine cancer, ovary cancer, skin cancer, leukemia, malignant lymphoma, epithelial malignant tumors, and non-epithelial malignant tumors.

In certain embodiments, a combination of therapeutic molecules of this invention can be used for silencing or inhibiting p21 gene expression.

This invention provides a range of RNAi molecules, where each molecule has a polynucleotide sense strand and a polynucleotide antisense strand; each strand of the molecule is from 15 to 30 nucleotides in length; a contiguous region of from 15 to 30 nucleotides of the antisense strand is complementary to a sequence of an mRNA encoding p21; and at least a portion of the sense strand is complementary to at least a portion of the antisense strand, and the molecule has a duplex region of from 15 to 30 nucleotides in length.

A RNAi molecule of this invention can have a contiguous region of from 15 to 30 nucleotides of the antisense strand that is complementary to a sequence of an mRNA encoding p21, which is located in the duplex region of the molecule.

In some embodiments, a RNAi molecule can have a contiguous region of from 15 to 30 nucleotides of the antisense strand that is complementary to a sequence of an mRNA encoding p21.

Embodiments of this invention may further provide methods for preventing, treating or ameliorating one or more symptoms of malignant tumor, or reducing the risk of developing malignant tumor, or delaying the onset of malignant tumor in a mammal in need thereof.

P21 and RNAi Molecules p21 is present in various animals including humans. Sequence information for human CDKN1A (p21) is found at: NM_000389.4, NM_078467.2, NM_001291549.1, NM_001220778.1, NM_001220777.1 (NP_001207707.1, NP_001278478.1, NP_001207706.1, NP_510867.1, NP_000380.1).

The target human p21 mRNA is disclosed in GenBank accession number NM_000389.4 (CDKN1A), and is 2175 base pairs in length.

One of ordinary skill in the art would understand that a reported sequence may change over time and to incorporate any changes needed in the nucleic acid molecules herein accordingly.

Embodiments of this invention can provide compositions and methods for gene silencing of p21 expression using small nucleic acid molecules. Examples of nucleic acid molecules include molecules active in RNA interference (RNAi molecules), short interfering RNA (siRNA), microRNA (miRNA), and short hairpin RNA (shRNA) molecules, as well as DNA-directed RNA (ddRNA), Piwi-interacting RNA (piRNA), and repeat associated siRNA (rasiRNA). Such molecules are capable of mediating RNA interference against p21 gene expression.

The composition and methods disclosed herein can also be used in treating various kinds of malignant tumors in a subject.

The nucleic acid molecules and methods of this invention may be used to down regulate the expression of genes that encode p21.

The compositions and methods of this invention can include one or more nucleic acid molecules, which, independently or in combination, can modulate or regulate the expression of p21 protein and/or genes encoding p21 proteins, proteins and/or genes encoding p21 associated with the maintenance and/or development of diseases, conditions or disorders associated with p21, such as malignant tumor.

The compositions and methods of this invention are described with reference to exemplary sequences of p21. A person of ordinary skill in the art would understand that various aspects and embodiments of the invention are directed to any related p21 genes, sequences, or variants, such as homolog genes and transcript variants, and polymorphisms, including single nucleotide polymorphism (SNP) associated with any p21 genes.

In some embodiments, the compositions and methods of this invention can provide a double-stranded short interfering nucleic acid (siRNA) molecule that downregulates the expression of a p21 gene, for example human CDKN1A.

A RNAi molecule of this invention can be targeted to p21 and any homologous sequences, for example, using complementary sequences or by incorporating non-canonical base pairs, for example, mismatches and/or wobble base pairs, that can provide additional target sequences.

In instances where mismatches are identified, non-canonical base pairs, for example, mismatches and/or wobble bases can be used to generate nucleic acid molecules that target more than one gene sequence.

For example, non-canonical base pairs such as UU and CC base pairs can be used to generate nucleic acid molecules that are capable of targeting sequences for differing p21 targets that share sequence homology. Thus, a RNAi molecule can be targeted to a nucleotide sequence that is conserved between homologous genes, and a single RNAi molecule can be used to inhibit expression of more than one gene.

In some aspects, the compositions and methods of this invention include RNAi molecules that are active against p21 mRNA, where the RNAi molecule includes a sequence complementary to any mRNA encoding a p21 sequence.

In some embodiments, a RNAi molecule of this disclosure can have activity against p21 RNA, where the RNAi molecule includes a sequence complementary to an RNA having a variant p21 encoding sequence, for example, a mutant p21 gene known in the art to be associated with malignant tumor.

In further embodiments, a RNAi molecule of this invention can include a nucleotide sequence that can interact with a nucleotide sequence of a p21 gene and mediate silencing of p21 gene expression.

The nucleic acid molecules for inhibiting expression of p21 may have a sense strand and an antisense strand, wherein the strands form a duplex region. The nucleic acid molecules may have one or more of the nucleotides in the duplex region being modified or chemically-modified, including such modifications as are known in the art. Any nucleotide in an overhang of the siRNA may also be modified or chemically-modified.

In some embodiments, the preferred modified or chemically-modified nucleotides are 2'-deoxy nucleotides. In additional embodiments, the modified or chemically-modified nucleotides can include 2'-O-alkyl substituted nucleotides, 2'-deoxy-2'-fluoro substituted nucleotides, phosphorothioate nucleotides, locked nucleotides, or any combination thereof.

In certain embodiments, a preferred structure can have an antisense strand containing deoxynucleotides in a plurality of positions, the plurality of positions being one of the following: each of positions 4, 6 and 8, from the 5' end of the antisense strand; each of positions 3, 5 and 7, from the 5' end of the antisense strand; each of positions 1, 3, 5 and 7, from the 5' end of the antisense strand; each of positions 3-8, from the 5' end of the antisense strand; and each of positions 5-8, from the 5' end of the antisense strand. Any of these structures can be combined with one or more 2'-deoxy-2'-fluoro substituted nucleotides in the duplex region.

The nucleic acid molecules of this invention can inhibit expression of p21 mRNA with an advantageous IC50 of less than about 200 pM. Further, the nucleic acid molecules can inhibit expression of p21 mRNA levels by at least 25% in vivo, upon a single administration.

Pharmaceutical compositions are contemplated in this invention, which can contain one or more siRNAs as described herein, in combination with a pharmaceutically acceptable carrier. Any suitable carrier may be used, including those known in the art, as well as lipid molecules, nanoparticles, or liposomes, any of which may encapsulate the siRNA molecules.

This invention discloses methods for treating a disease that may be associated with p21 expression, which methods include administering to a subject in need a composition containing one or more of the siRNAs. Diseases to be treated may include malignant tumor, cancer, cancer caused by cells expressing mutated KRAS, sarcoma, and carcinoma, among others.

Examples of RNAi molecules of this invention targeted to p21 mRNA are shown in Table 1.

TABLE 1

RNAi molecule sequences for p21

| Ref Pos | SEQ ID NO | SENSE STRAND (5'-->3') SEQ ID NOS: 1 to 28 | SEQ ID NO | ANTISENSE STRAND (5'-->3') SEQ ID NOS: 29 to 56 |
|---|---|---|---|---|
| 2085 | 1 | CUUAGUGACUUUACUUGU AmUmU | 29 | UACAAGUAAAGUCACU AAGmUmU |
| 500 | 2 | CAGACCAGCAUGACAGAU UmUmU | 30 | AAUCUGUCAUGCUGGU CUGmUmU |
| 540 | 3 | UGAUCUUCUCCAAGAGGA AmUmU | 31 | UUCCUCUUGGAGAAGA UCAmUmU |
| 1706 | 4 | GUUCAUUGCACUUUGAUU AmUmU | 32 | UAAUCAAAGUGCAAUG AACmUmU |
| 1709 | 5 | CAUUGCACUUUGAUUAGC AmUmU | 33 | UGCUAAUCAAAGUGCA AUGmUmU |
| 210 | 6 | AGCGAUGGAACUUCGACU UmUmU | 34 | AAGUCGAAGUUCCAUC GCUmUmU |
| 211 | 7 | GCGAUGGAACUUCGACUU UmUmU | 35 | AAAGUCGAAGUUCCAU CGCmUmU |
| 1473 | 8 | GGGAAGGGACACACAAGA AmUmU | 36 | UUCUUGUGUGUCCCUU CCCmUmU |
| 1507 | 9 | UCUACCUCAGGCAGCUCA AmUmU | 37 | UUGAGCUGCCUGAGGU AGAmUmU |
| 2067 | 10 | GGUGCUCAAUAAAUGAUU CmUmU | 38 | GAAUCAUUUAUUGAGC ACCmUmU |
| 1063 | 11 | CAUCAUCAAAAACUUUGG AmUmU | 39 | UCCAAAGUUUUUGAUG AUGmUmU |
| 1735 | 12 | AAGGAGUCAGACAUUUUA AmUmU | 40 | UUAAAAUGUCUGACUC CUUmUmU |
| 783 | 13 | GUGCUGGGCAUUUUUAUU UmUmU | 41 | AAAUAAAAAUGCCCAG CACmUmU |
| 869 | 14 | GCCGGCUUCAUGCCAGCU AmUmU | 42 | UAGCUGGCAUGAAGCC GGCmUmU |
| 1060 | 15 | GGGCAUCAUCAAAAACUU UmUmU | 43 | AAAGUUUUUGAUGAUG CCCmUmU |
| 1492 | 16 | GAAGGGCACCCUAGUUCU AmUmU | 44 | UAGAACUAGGGUGCCC UUCmUmU |
| 1704 | 17 | CAGUUCAUUGCACUUUGA UmUmU | 45 | AUCAAAGUGCAAUGAA CUGmUmU |
| 1733 | 18 | ACAAGGAGUCAGACAUUU UmUmU | 46 | AAAAUGUCUGACUCCU UGUmUmU |
| 1847 | 19 | UGGAGGCACUGAAGUGCU UmUmU | 47 | AAGCACUUCAGUGCCU CCAmUmU |
| 2000 | 20 | GCAGGGACCACACCCUGU AmUmU | 48 | UACAGGGUGUGGUCCC UGCmUmU |
| 2014 | 21 | CUGUACUGUUCUGUGUCU UmUmU | 49 | AAGACACAGAACAGUA CAGmUmU |
| 677 | 22 | UUAAACACCUCCUCAUGU AmUmU | 50 | UACAUGAGGAGGUGUU UAAmUmU |
| 475 | 23 | AGACUCUCAGGGUCGAAA AmUmU | 51 | UUUUCGACCCUGAGAG UCUmUmU |
| 508 | 24 | CAUGACAGAUUUCUACCA CmUmU | 52 | GUGGUAGAAAUCUGUC AUGmUmU |
| 514 | 25 | AGAUUUCUACCACUCCAA AmUmU | 53 | UUUGGAGUGGUAGAAA UCUmUmU |
| 549 | 26 | CCAAGAGGAAGCCCUAAU CmUmU | 54 | GAUUAGGGCUUCCUCU UGGmUmU |
| 382 | 27 | GACAGCAGAGGAAGACCA UmUmU | 55 | AUGGUCUUCCUCUGCU GUCmUmU |
| 2042 | 28 | CUCCCACAAUGCUGAAUA UmUmU | 56 | AUAUUCAGCAUUGUGG GAGmUmU |

Key for Table 1: Upper case A, G, C and U referred to for ribo-A, ribo-G, ribo-C and ribo-U respectively. The lower case letters a, g, c, t represent 2'-deoxy-A, 2'-deoxy-G, 2'-deoxy-C and thymidine respectively. mU is 2'-methoxy-U.

Examples of RNAi molecules of this invention targeted to p21 mRNA are shown in Table 2.

TABLE 2

RNAi molecule sequences for p21

| Ref Pos | SEQ ID NO | SENSE STRAND (5'-->3') SEQ ID NOS: 57 to 70 | SEQ ID NO | ANTISENSE STRAND (5'-->3') SEQ ID NOS: 71 to 84 |
|---|---|---|---|---|
| 1735' | 57 | AAGGAGUCAGAC AUUUUAANN | 71 | UUAAAAUGUCUGACUC CUUNN |
| 1 | 58 | <u>AA</u>GGAGU<u>C</u>AGA<u>C</u> AUUU<u>U</u>AA<u>UU</u> | 72 | UUAaAaUgUC<u>U</u>GACUC CU<u>UUU</u> |
| 2 | 59 | <u>AA</u>GGAGU<u>C</u>AGAC AUUU<u>U</u>AA<u>UU</u> | 73 | UUAaAaUgUC<u>U</u>GACUC CU<u>UUU</u> |
| 3 | 60 | <u>AA</u>GGAGU<u>C</u>AGA<u>C</u> AUUU<u>U</u>AA<u>UU</u> | 74 | UUAaAaUgUCUGACUC CU<u>UUU</u> |
| 4 | 61 | <u>AA</u>GGAGU<u>C</u>AGA<u>C</u> AUUU<u>U</u>AA<u>UU</u> | 75 | UUAaAaUgUC<u>U</u>GACUC CU<u>UUU</u> |
| 5 | 62 | AAGGAGUCAGAC AUUU<u>U</u>A<u>UU</u> | 76 | UUaaaaugUCUGACUC CU<u>UUU</u> |
| 6 | 63 | AAGGAGUCAGAC AUUU<u>U</u>A<u>UU</u> | 77 | UUAAaaugUCUGACUC CU<u>UUU</u> |
| 7 | 64 | AAGGAGUCAGAC AUUU<u>U</u>A<u>UU</u> | 78 | uUaAaAuGUCUGACUC CU<u>UUU</u> |
| 8 | 65 | AAGGAGUCAGAC AUUU<u>U</u>AA<u>UU</u> | 79 | UUaAaAuGUCUGACUC CU<u>UUU</u> |
| 9 | 66 | AAGGAGUCAGAC AUUU<u>U</u>AA<u>UU</u> | 80 | UUAaAaUgUCUGACUC CU<u>UUU</u> |
| 10 | 67 | AAGGAGUCAGAC AUUU<u>U</u>A<u>UU</u> | 81 | U<u>U</u>AAA<u>AU</u>GUC<u>U</u>GACUC CU<u>UUU</u> |
| 11 | 68 | AAGGAGU<u>C</u>AGA<u>C</u> AUUU<u>U</u>AA<u>UU</u> | 82 | UUAAAAUGUCUGACUC CU<u>UUU</u> |
| 12 | 69 | <u>A</u>AGGAGUCAGAC AUUU<u>U</u>AA<u>UU</u> | 83 | UUAAAAUGUCUGACUC CU<u>UUU</u> |
| 13 | 70 | <u>AA</u>GGAGU<u>C</u>AGA<u>C</u> AUUU<u>U</u>AA<u>UU</u> | 84 | UUAAAAUGUCUGACUC CU<u>UUU</u> |

Key for Table 2: Upper case A, G, C and U refer to ribo-A, ribo-G, ribo-C and ribo-U, respectively. The lower case letters a, u, g, c, t refer to 2'-deoxy-A, 2'-deoxy-U, 2'-deoxy-G, 2'-deoxy-C, and deoxythymidine (dT=T=t) respectively. Underlining refers to 2'-OMe-substituted, e.g., <u>U</u>. N is A, C, G, U, <u>U</u>, a, c, g, u, t, or a modified, inverted, or chemically modified nucleotide.

In some embodiments, this invention provides a range of nucleic acid molecules, where a) the molecule has a polynucleotide sense strand and a polynucleotide antisense strand; b) each strand of the molecule is from 15 to 30 nucleotides in length; c) a contiguous region of from 15 to 30 nucleotides of the antisense strand is complementary to a sequence of an mRNA encoding p21; and d) at least a portion of the sense strand is complementary to at least a portion of the antisense strand, and the molecule has a duplex region of from 15 to 30 nucleotides in length.

In some embodiments, the nucleic acid molecule can have a contiguous region of from 15 to 30 nucleotides of the antisense strand that is complementary to a sequence of an mRNA encoding p21, and is located in the duplex region of the molecule.

In additional embodiments, the nucleic acid molecule can have a contiguous region of from 15 to 30 nucleotides of the antisense strand that is complementary to a sequence of an mRNA encoding p21.

In further aspects, a nucleic acid molecule of this invention can have each strand of the molecule being from 18 to 22 nucleotides in length. A nucleic acid molecule can have a duplex region of 19 nucleotides in length.

In certain embodiments, a nucleic acid molecule can have a polynucleotide sense strand and the polynucleotide antisense strand that are connected as a single strand, and form a duplex region connected at one end by a loop.

The nucleic acid molecules of this invention can have a blunt end, and can have one or more 3' overhangs.

The nucleic acid molecules of this invention can be RNAi molecules that are active for gene silencing, for example, a dsRNA that is active for gene silencing, a siRNA, a microRNA, or a shRNA active for gene silencing, as well as a DNA-directed RNA (ddRNA), a Piwi-interacting RNA (piRNA), and a repeat associated siRNA (rasiRNA).

This invention provides a range of nucleic acid molecules that are active for inhibiting expression of p21. In some embodiments, the nucleic acid molecule can have an IC50 for knockdown of p21 of less than 100 pM.

In additional embodiments, the nucleic acid molecule can have an IC50 for knockdown of p21 of less than 50 pM.

This invention further contemplates compositions containing one or more inventive nucleic acid molecules and a pharmaceutically acceptable carrier. The carrier can be a lipid molecule or liposome.

The compounds and compositions of this invention are useful in methods for preventing or treating a p21 associated disease, by administering a compound or composition to a subject in need.

In further aspects, this invention includes methods for treating a disease associated with p21 expression, by administering to a subject in need a composition containing one or more inventive nucleic acid molecules. The disease can be malignant tumor, which may be presented in a disease such as cancers associated with p21 expression, among others.

The methods of this invention can utilize the inventive compounds for preventing or treating malignant tumor. The malignant tumor can be presented in various diseases, for example, cancers associated with p21 expression, cancers caused by cells expressing mutated KRAS, sarcomas, fibrosarcoma, malignant fibrous histiocytoma, liposarcoma, rhabdomyosarcoma, leiomyosarcoma, angiosarcoma, Kaposi's sarcoma, lymphangiosarcoma, synovial sarcoma, chondrosarcoma, osteosarcoma, carcinomas, brain tumor, head and neck cancer, breast cancer, lung cancer, esophageal cancer, stomach cancer, duodenal cancer, appendix cancer, colorectal cancer, rectal cancer, liver cancer, pancreatic cancer, gallbladder cancer, bile duct cancer, kidney cancer, urethral cancer, urinary bladder cancer, prostate cancer, testicular cancer, uterine cancer, ovary cancer, skin cancer, leukemia, malignant lymphoma, epithelial malignant tumors, and non-epithelial malignant tumors.

Modified and Chemically-Modified siRNAs

Embodiments of this invention encompass siRNA molecules that are modified or chemically-modified to provide enhanced properties for therapeutic use, such as increased activity and potency for gene silencing. This invention provides modified or chemically-modified siRNA molecules that can have increased serum stability, as well as reduced off target effects, without loss of activity and potency of the siRNA molecules for gene modulation and gene silencing. In some aspects, this invention provides siRNAs having modifications or chemical modifications in various combinations, which enhance the stability and efficacy of the siRNA.

As used herein, the terms modified and chemically-modified refer to changes made in the structure of a naturally-occurring nucleotide or nuclei acid structure of an siRNA, which encompasses siRNAs having one or more nucleotide analogs, altered nucleotides, non-standard nucleotides, non-naturally occurring nucleotides, and combinations thereof.

In some embodiments, the number of modified or chemically-modified structures in an siRNA can include all of the structural components, and/or all of the nucleotides of the siRNA molecule.

Examples of modified and chemically-modified siRNAs include siRNAs having modification of the sugar group of a nucleotide, modification of a nucleobase of a nucleotide, modification of a nucleic acid backbone or linkage, modification of the structure of a nucleotide or nucleotides at the terminus of a siRNA strand, and combinations thereof.

Examples of modified and chemically-modified siRNAs include siRNAs having modification of the substituent at the 2' carbon of the sugar.

Examples of modified and chemically-modified siRNAs include siRNAs having modification at the 5' end, the 3' end, or at both ends of a strand.

Examples of modified and chemically-modified siRNAs include siRNAs having modifications that produce complementarity mismatches between the strands.

Examples of modified and chemically-modified siRNAs include siRNAs having a 5'-propylamine end, a 5'-phosphorylated end, a 3'-puromycin end, or a 3'-biotin end group.

Examples of modified and chemically-modified siRNAs include siRNAs having a 2'-fluoro substituted ribonucleotide, a 2'-OMe substituted ribonucleotide, a 2'-deoxy ribonucleotide, a 2'-amino substituted ribonucleotide, a 2'-thio substituted ribonucleotide.

Examples of modified and chemically-modified siRNAs include siRNAs having one or more 5-halouridines, 5-halocytidines, 5-methylcytidines, ribothymidines, 2-aminopurines, 2,6-diaminopurines, 4-thiouridines, or 5-aminoallyluridines.

Examples of modified and chemically-modified siRNAs include siRNAs having one or more phosphorothioate groups.

Examples of modified and chemically-modified siRNAs include siRNAs having one or more 2'-fluoro substituted ribonucleotides, 2'-fluorouridines, 2'-fluorocytidines, 2'-deoxyribonucleotides, 2'-deoxyadenosines, or 2'-deoxyguanosines.

Examples of modified and chemically-modified siRNAs include siRNAs having one or more phosphorothioate linkages.

Examples of modified and chemically-modified siRNAs include siRNAs having one or more alkylene diol linkages, oxy-alkylthio linkages, or oxycarbonyloxy linkages.

Examples of modified and chemically-modified siRNAs include siRNAs having one or more deoxyabasic groups, inosines, N3-methyl-uridines, N6,N6-dimethyl-adenosines, pseudouridines, purine ribonucleosides, and ribavirins.

Examples of modified and chemically-modified siRNAs include siRNAs having one or more 3' or 5' inverted terminal groups.

Examples of modified and chemically-modified siRNAs include siRNAs having one or more 5-(2-amino)propyluridines, 5-bromouridines, adenosines, 8-bromo guanosines, 7-deaza-adenosines, or N6-methyl adenosine.

Methods for Modulating p21 and Treating Malignant Tumor

Embodiments of this invention can provide RNAi molecules that can be used to down regulate or inhibit the expression of p21 and/or p21 proteins.

In some embodiments, a RNAi molecule of this invention can be used to down regulate or inhibit the expression of CDKN1A and/or p21 proteins arising from CDKN1A haplotype polymorphisms that may be associated with a disease or condition such as malignant tumor.

Monitoring of p21 protein or mRNA levels can be used to characterize gene silencing, and to determine the efficacy of compounds and compositions of this invention.

The RNAi molecules of this disclosure can be used individually, or in combination with other siRNAs for modulating the expression of one or more genes.

The RNAi molecules of this disclosure can be used individually, or in combination, or in conjunction with other known drugs for preventing or treating diseases, or ameliorating symptoms of conditions or disorders associated with p21, including malignant tumor.

The RNAi molecules of this invention can be used to modulate or inhibit the expression of p21 in a sequence-specific manner.

The RNAi molecules of this disclosure can include a guide strand for which a series of contiguous nucleotides are at least partially complementary to a p21 mRNA.

In certain aspects, malignant tumor may be treated by RNA interference using a RNAi molecule of this invention.

Treatment of malignant tumor may be characterized in suitable cell-based models, as well as ex vivo or in vivo animal models.

Treatment of malignant tumor may be characterized by non-invasive medical scanning of an affected organ or tissue.

Embodiments of this invention may include methods for preventing, treating, or ameliorating the symptoms of a p21 associated disease or condition in a subject in need thereof.

In some embodiments, methods for preventing, treating, or ameliorating the symptoms of malignant tumor in a subject can include administering to the subject a RNAi molecule of this invention to modulate the expression of a CDKN1A gene (p21) in the subject or organism.

In some embodiments, this invention contemplates methods for down regulating the expression of a CDKN1A gene (p21) in a cell or organism, by contacting the cell or organism with a RNAi molecule of this invention.

Embodiments of this invention encompass siRNA molecules of Tables 1 and 2 that are modified or chemically-modified according to the examples above.

RNA Interference

RNA interference (RNAi) refers to sequence-specific post-transcriptional gene silencing in animals mediated by short interfering RNAs (siRNAs). See, e.g., Zamore et al., Cell, 2000, Vol. 101, pp. 25-33; Fire et al., Nature, 1998, Vol. 391, pp. 806811; Sharp, Genes & Development, 1999, Vol. 13, pp. 139-141.

An RNAi response in cells can be triggered by a double stranded RNA (dsRNA), although the mechanism is not yet fully understood. Certain dsRNAs in cells can undergo the action of Dicer enzyme, a ribonuclease III enzyme. See, e.g., Zamore et al., Cell, 2000, Vol. 101, pp. 25-33; Hammond et al., Nature, 2000, Vol. 404, pp. 293-296. Dicer can process the dsRNA into shorter pieces of dsRNA, which are siRNAs.

In general, siRNAs can be from about 21 to about 23 nucleotides in length and include a base pair duplex region about 19 nucleotides in length.

RNAi involves an endonuclease complex known as the RNA induced silencing complex (RISC). An siRNA has an antisense or guide strand which enters the RISC complex and mediates cleavage of a single stranded RNA target having a sequence complementary to the antisense strand of the siRNA duplex. The other strand of the siRNA is the passenger strand. Cleavage of the target RNA takes place in the middle of the region complementary to the antisense strand of the siRNA duplex See, e.g., Elbashir et al., Genes & Development, 2001, Vol. 15, pp. 188-200.

As used herein, the term "sense strand" refers to a nucleotide sequence of a siRNA molecule that is partially or fully complementary to at least a portion of a corresponding antisense strand of the siRNA molecule. The sense strand of a siRNA molecule can include a nucleic acid sequence having homology with a target nucleic acid sequence.

As used herein, the term "antisense strand" refers to a nucleotide sequence of a siRNA molecule that is partially or fully complementary to at least a portion of a target nucleic acid sequence. The antisense strand of a siRNA molecule can include a nucleic acid sequence that is complementary to at least a portion of a corresponding sense strand of the siRNA molecule.

RNAi molecules can down regulate or knock down gene expression by mediating RNA interference in a sequence-specific manner. See, e.g., Zamore et al., Cell, 2000, Vol. 101, pp. 25-33; Elbashir et al., Nature, 2001, Vol. 411, pp. 494-498; Kreutzer et al., WO2000/044895; Zernicka-Goetz et al., WO2001/36646; Fire et al., WO1999/032619; Plaetinck et al., WO2000/01846; Mello et al., WO2001/029058.

As used herein, the terms "inhibit," "down-regulate," or "reduce" with respect to gene expression means that the expression of the gene, or the level of mRNA molecules encoding one or more proteins, or the activity of one or more of the encoded proteins is reduced below that observed in the absence of a RNAi molecule or siRNA of this invention. For example, the level of expression, level of mRNA, or level of encoded protein activity may be reduced by at least 1%, or at least 10%, or at least 20%, or at least 50%, or at least 90%, or more from that observed in the absence of a RNAi molecule or siRNA of this invention.

RNAi molecules can also be used to knock down viral gene expression, and therefore affect viral replication.

RNAi molecules can be made from separate polynucleotide strands: a sense strand or passenger strand, and an antisense strand or guide strand. The guide and passenger strands are at least partially complementary. The guide strand and passenger strand can form a duplex region having from about 15 to about 49 base pairs.

In some embodiments, the duplex region of a siRNA can have 17, 18, 19, 20, 21, 22, 23, 24, 25, 26, 27, 28, 29, 30, 31, 32, 33, 34, 35, 36, 37, 38, 39, 40, 41, 42, 43, 44, 45, 46, 47, 48, or 49 base pairs.

In certain embodiments, a RNAi molecule can be active in a RISC complex, with a length of duplex region active for RISC.

In additional embodiments, a RNAi molecule can be active as a Dicer substrate, to be converted to a RNAi molecule that can be active in a RISC complex.

In some aspects, a RNAi molecule can have complementary guide and passenger sequence portions at opposing ends of a long molecule, so that the molecule can form a duplex region with the complementary sequence portions, and the strands are linked at one end of the duplex region by either nucleotide or non-nucleotide linkers. For example, a hairpin arrangement, or a stem and loop arrangement. The linker interactions with the strands can be covalent bonds or non-covalent interactions.

A RNAi molecule of this disclosure may include a nucleotide, non-nucleotide, or mixed nucleotide/non-nucleotide linker that joins the sense region of the nucleic acid to the antisense region of the nucleic acid. A nucleotide linker can be a linker of ≥2 nucleotides in length, for example about 3, 4, 5, 6, 7, 8, 9, or 10 nucleotides in length. The nucleotide linker can be a nucleic acid aptamer. By "aptamer" or "nucleic acid aptamer" as used herein refers to a nucleic acid molecule that binds specifically to a target molecule wherein the nucleic acid molecule has sequence that includes a sequence recognized by the target molecule in its natural setting. Alternately, an aptamer can be a nucleic acid molecule that binds to a target molecule, where the target molecule does not naturally bind to a nucleic acid. For example, the aptamer can be used to bind to a ligand-binding domain of a protein, thereby preventing interaction of the naturally occurring ligand with the protein. See, e.g., Gold et al., Annu Rev Biochem, 1995, Vol. 64, pp. 763-797; Brody et al., J. Biotechnol., 2000, Vol. 74, pp. 5-13; Hermann et al., Science, 2000, Vol. 287, pp. 820-825.

Examples of a non-nucleotide linker include an abasic nucleotide, polyether, polyamine, polyamide, peptide, carbohydrate, lipid, polyhydrocarbon, or other polymeric compounds, for example polyethylene glycols such as those having from 2 to 100 ethylene glycol units. Some examples are described in Seela et al., Nucleic Acids Research, 1987, Vol. 15, pp. 3113-3129; Cload et al., J. Am. Chem. Soc., 1991, Vol. 113, pp. 6324-6326; Jaeschke et al., Tetrahedron Lett., 1993, Vol. 34, pp. 301; Arnold et al., WO1989/002439; Usman et al., WO1995/006731; Dudycz et al., WO1995/011910, and Ferentz et al., J. Am. Chem. Soc., 1991, Vol. 113, pp. 4000-4002.

A RNAi molecule can have one or more overhangs from the duplex region. The overhangs, which are non-base-paired, single strand regions, can be from one to eight nucleotides in length, or longer. An overhang can be a 3'-end overhang, wherein the 3'-end of a strand has a single strand region of from one to eight nucleotides. An overhang can be a 5'-end overhang, wherein the 5'-end of a strand has a single strand region of from one to eight nucleotides.

The overhangs of a RNAi molecule can have the same length, or can be different lengths.

A RNAi molecule can have one or more blunt ends, in which the duplex region ends with no overhang, and the strands are base paired to the end of the duplex region.

A RNAi molecule of this disclosure can have one or more blunt ends, or can have one or more overhangs, or can have a combination of a blunt end and an overhang end.

A 5'-end of a strand of a RNAi molecule may be in a blunt end, or can be in an overhang. A 3'-end of a strand of a RNAi molecule may be in a blunt end, or can be in an overhang.

A 5'-end of a strand of a RNAi molecule may be in a blunt end, while the 3'-end is in an overhang. A 3'-end of a strand of a RNAi molecule may be in a blunt end, while the 5'-end is in an overhang.

In some embodiments, both ends of a RNAi molecule are blunt ends.

In additional embodiments, both ends of a RNAi molecule have an overhang.

The overhangs at the 5'- and 3'-ends may be of different lengths.

In certain embodiments, a RNAi molecule may have a blunt end where the 5'-end of the antisense strand and the 3'-end of the sense strand do not have any overhanging nucleotides.

In further embodiments, a RNAi molecule may have a blunt end where the 3'-end of the antisense strand and the 5'-end of the sense strand do not have any overhanging nucleotides.

A RNAi molecule may have mismatches in base pairing in the duplex region.

Any nucleotide in an overhang of a RNAi molecule can be a deoxyribonucleotide, or a ribonucleotide.

One or more deoxyribonucleotides may be at the 5'-end, where the 3'-end of the other strand of the RNAi molecule may not have an overhang, or may not have a deoxyribonucleotide overhang.

One or more deoxyribonucleotides may be at the 3'-end, where the 5'-end of the other strand of the RNAi molecule may not have an overhang, or may not have a deoxyribonucleotide overhang.

In some embodiments, one or more, or all of the overhang nucleotides of a RNAi molecule may be 2'-deoxyribonucleotides.

Dicer Substrate RNAi Molecules

In some aspects, a RNAi molecule can be of a length suitable as a Dicer substrate, which can be processed to produce a RISC active RNAi molecule. See, e.g., Rossi et al., US2005/0244858.

A double stranded RNA (dsRNA) that is a Dicer substrate can be of a length sufficient such that it is processed by Dicer to produce an active RNAi molecule, and may further include one or more of the following properties: (i) the Dicer substrate dsRNA can be asymmetric, for example, having a 3' overhang on the antisense strand, and (ii) the Dicer substrate dsRNA can have a modified 3' end on the sense strand to direct orientation of Dicer binding and processing of the dsRNA to an active RNAi molecule.

In certain embodiments, the longest strand in a Dicer substrate dsRNA may be 24-30 nucleotides in length.

A Dicer substrate dsRNA can be symmetric or asymmetric.

In some embodiments, a Dicer substrate dsRNA can have a sense strand of 22-28 nucleotides and an antisense strand of 24-30 nucleotides.

In certain embodiments, a Dicer substrate dsRNA may have an overhang on the 3' end of the antisense strand.

In further embodiments, a Dicer substrate dsRNA may have a sense strand 25 nucleotides in length, and an antisense strand 27 nucleotides in length, with a 2 base 3'-overhang. The overhang may be 1, 2 or 3 nucleotides in length. The sense strand may also have a 5' phosphate.

An asymmetric Dicer substrate dsRNA may have two deoxyribonucleotides at the 3'-end of the sense strand in place of two of the ribonucleotides.

The sense strand of a Dicer substrate dsRNA may be from about 22 to about 30, or from about 22 to about 28; or from about 24 to about 30; or from about 25 to about 30; or from about 26 to about 30; or from about 26 and 29; or from about 27 to about 28 nucleotides in length.

The sense strand of a Dicer substrate dsRNA may be 22, 23, 24, 25, 26, 27, 28, 29 or 30 nucleotides in length.

In certain embodiments, a Dicer substrate dsRNA may have sense and antisense strands that are at least about 25 nucleotides in length, and no longer than about 30 nucleotides in length.

In certain embodiments, a Dicer substrate dsRNA may have sense and antisense strands that are 26 to 29 nucleotides in length.

In certain embodiments, a Dicer substrate dsRNA may have sense and antisense strands that are 27 nucleotides in length.

The sense and antisense strands of a Dicer substrate dsRNA may be the same length as in being blunt ended, or different lengths as in having overhangs, or may have a blunt end and an overhang.

A Dicer substrate dsRNA may have a duplex region of 19, 20, 21, 22, 23, 24, 25, 26 or 27 nucleotides in length.

The antisense strand of a Dicer substrate dsRNA may have any sequence that anneals to at least a portion of the sequence of the sense strand under biological conditions, such as within the cytoplasm of a eukaryotic cell.

A Dicer substrate with a sense and an antisense strand can be linked by a third structure, such as a linker group or a linker oligonucleotide. The linker connects the two strands of the dsRNA, for example, so that a hairpin is formed upon annealing.

The sense and antisense strands of a Dicer substrate are in general complementary, but may have mismatches in base pairing.

In some embodiments, a Dicer substrate dsRNA can be asymmetric such that the sense strand has 22-28 nucleotides and the antisense strand has 24-30 nucleotides.

A region of one of the strands, particularly the antisense strand, of the Dicer substrate dsRNA may have a sequence length of at least 19 nucleotides, wherein these nucleotides are in the 21-nucleotide region adjacent to the 3' end of the antisense strand and are sufficiently complementary to a nucleotide sequence of the RNA produced from the target gene.

An antisense strand of a Dicer substrate dsRNA can have from 1 to 9 ribonucleotides on the 5'-end, to give a length of 22-28 nucleotides. When the antisense strand has a length of 21 nucleotides, then 1-7 ribonucleotides, or 2-5 ribonucleotides, or 4 ribonucleotides may be added on the 3'-end. The added ribonucleotides may have any sequence.

A sense strand of a Dicer substrate dsRNA may have 24-30 nucleotides. The sense strand may be substantially complementary with the antisense strand to anneal to the antisense strand under biological conditions.

Methods of Use of RNAi Molecules

The nucleic acid molecules and RNAi molecules of this invention may be delivered to a cell or tissue by direct application of the molecules, or with the molecules combined with a carrier or a diluent.

The nucleic acid molecules and RNAi molecules of this invention can be delivered or administered to a cell, tissue, organ, or subject by direct application of the molecules with a carrier or diluent, or any other delivery vehicle that acts to assist, promote or facilitate entry into a cell, for example, viral sequences, viral material, or lipid or liposome formulations.

The nucleic acid molecules and RNAi molecules of this invention can be complexed with cationic lipids, packaged within liposomes, or otherwise delivered to target cells or tissues. The nucleic acid or nucleic acid complexes can be locally administered to relevant tissues ex vivo, or in vivo through direct dermal application, transdermal application, or injection.

Delivery systems may include, for example, aqueous and nonaqueous gels, creams, emulsions, microemulsions, liposomes, ointments, aqueous and nonaqueous solutions, lotions, aerosols, hydrocarbon bases and powders, and can contain excipients such as solubilizers and permeation enhancers.

Compositions and methods of this disclosure can include an expression vector that includes a nucleic acid sequence encoding at least one RNAi molecule of this invention in a manner that allows expression of the nucleic acid molecule.

The nucleic acid molecules and RNAi molecules of this invention can be expressed from transcription units inserted into DNA or RNA vectors. Recombinant vectors can be DNA plasmids or viral vectors. Viral vectors can be used that provide for transient expression of nucleic acid molecules.

For example, the vector may contain sequences encoding both strands of a RNAi molecule of a duplex, or a single nucleic acid molecule that is self-complementary and thus forms a RNAi molecule. An expression vector may include a nucleic acid sequence encoding two or more nucleic acid molecules.

A nucleic acid molecule may be expressed within cells from eukaryotic promoters. Those skilled in the art realize that any nucleic acid can be expressed in eukaryotic cells from the appropriate DNA/RNA vector.

In some aspects, a viral construct can be used to introduce an expression construct into a cell, for transcription of a dsRNA construct encoded by the expression construct.

Lipid formulations can be administered to animals by intravenous, intramuscular, or intraperitoneal injection, or orally or by inhalation or other methods as are known in the art.

Pharmaceutically acceptable formulations for administering oligonucleotides are known and can be used.

Example Protocol for In Vitro Knockdown

One day before the transfection, plate the cells in a 96-well plate at 2×103 cells per well with 100 µl of DMEM (HyClone Cat. # SH30243.01) containing 10% FBS and culture in a 37° C. incubator containing a humidified atmosphere of 5% CO2 in air. Before transfection, change medium to 90 µl of Opti-MEM I Reduced Serum Medium (Life Technologies Cat. #31985-070) containing 2% FBS. Mix 0.2 µl of Lipofectamine RNAiMax (Life Technologies Cat. #13778-100) with 4.8 µl of Opti-MEM I for 5 minutes at room temperature. Mix 1 µl of siRNA with 4 µl of Opti-MEM I and combine with the LF2000 solution and then mix gently, without vortex. Wait for 5 minutes at room temperature. Incubate the mixture for 10 minutes at room temperature to allow the RNA-RNAiMax complexes to form. Add the 10 µl of RNA-RNAiMax complexes to a well and shake the plate gently by hand. Incubate the cells in a 37° C. incubator containing a humidified atmosphere of 5% CO2 in air for 2 hours. Change medium to fresh-MEM I Reduced Serum Medium (Life Technologies Cat. #31985-070) containing 2% FBS. 24 hours after transfection, wash the cells with ice-cold PBS once. Lyse the cells with 50 µl of Cell-to-Ct Lysis Buffer (Life Technologies Cat. #4391851 C) for 5-30 minutes at room temperature. Add 5 µl of Stop Solution and incubate for 2 minutes at room temperature. Measure mRNA level by RT-qPCR with TAQMAN immediately. Alternatively, the samples can be frozen at −80° C. and assayed at a later time.

The positive control for the screening measurement was a molecule having the sense and antisense strand pair as follows.

```
                                           SEQ ID NO: 85
    Sense:     UCCUAAGAGUGCUGGGCAUdTdT SEQ ID NO: 86
    Antisense: AUGCCCAGCACUCUUAGGAdTdT.
```

Example Protocol for Serum Stability 0.2 mg/ml siRNA was incubated with 10% human serum at 37° C. At certain time points (0, 5, 15 and 30 min), 200 µl of sample was aliquoted and extracted with 200 µl extraction solvent (Chloroform:phenol:Isoamyl alcohol=24:25:1). The sample was vortexed and centrifuged at 13,000 rpm for 10 min at RT, then the top layer solution was transferred and filtered it with 0.45 µm filter. The filtrate was transferred into a 300 µl HPLC injection vial. For LCMS, the Mobile phase was MPA: 100 mM HFIP+7 mM TEA in H2O, MPB: 50% Methanol+50% Acetonitrile. The Column:Waters Acquity OST 2.1×50 mm, 1.7 µm.

EXAMPLES

Example 1 siRNAs of this invention targeted to p21 were found to be active for gene silencing in vitro. The dose-dependent activities of p21 siRNAs for gene knockdown were found to exhibit an IC50 below about 3 picomolar (pM), and as low as 1 pM.

In vitro transfection was performed in an A549 cell line to determine siRNA knockdown efficacy. Dose dependent knockdown for p21 mRNA was observed with siRNAs of Table 1, as shown in Table 3.

TABLE 3

Dose dependent knockdown for p21 mRNA in an A549 cell line

| P21 siRNA structure | IC50 (pM) |
| --- | --- |
| 1735 (SEQ ID NOs: 12 and 40) | 0.3 |
| 2042 (SEQ ID NOs: 28 and 56) | 10 |

As shown in Table 3, the activities of p21 siRNAs of Table 1 were in the range 0.3-10 pM, which is suitable for many uses, including as a drug agent to be used in vivo.

Example 2

The structure of p21 siRNAs of this invention having deoxynucleotides located in the seed region of the antisense strand of the siRNA provided unexpectedly and advantageously increased gene knockdown activity.

In vitro transfection was performed in an A549 cell line to determine knockdown efficacy for p21 siRNAs based on structure 1735' (SEQ ID NOs:57 and 71). Dose dependent knockdown of p21 mRNA was observed with p21 siRNAs based on structure 1735' as shown in Table 4.

TABLE 4

Dose dependent knockdown of p21 mRNA in an A549 cell line for p21 siRNAs based on structure 1735'

| P21 siRNA structure | IC50 (pM) |
| --- | --- |
| 1735 with no deoxynucleotides in the duplex region (SEQ ID NOs: 12 and 40) | 0.3 |
| 1735 with deoxynucleotides in positions 4, 6, and 8 of the seed region antisense strand, and additional 2'-OMe nucleotides (SEQ ID NOs: 58 and 72) | 0.05 |

TABLE 4-continued

Dose dependent knockdown of p21 mRNA in an A549
cell line for p21 siRNAs based on structure 1735'

| P21 siRNA structure | IC50 (pM) |
|---|---|
| 1735 with deoxynucleotides in positions 4, 6, and 8 of the seed region antisense strand, and additional 2'-OMe nucleotides (SEQ ID NOs: 59 and 73) | 0.001 |
| 1735 with deoxynucleotides in positions 4, 6, and 8 of the seed region antisense strand, and additional 2'-OMe nucleotides (SEQ ID NOs: 60 and 74) | 0.1 |

As shown in Table 4, the activities of p21 siRNAs based on structure 1735' having three deoxynucleotides in the seed region of the antisense strand were surprisingly and unexpectedly increased by up to 300-fold, as compared to a p21 siRNA without deoxynucleotides in the duplex region.

These data show that p21 siRNAs having a structure with deoxynucleotides in the seed region of the antisense strand provided surprisingly increased gene knockdown activity as compared to a p21 siRNA without deoxynucleotides in the duplex region.

The activities shown in Table 4 for p21 siRNAs having three deoxynucleotides in the seed region of the antisense strand were in the range 0.001 to 0.1 pM, which is exceptionally suitable for many uses, including as a drug agent to be used in vivo.

The embodiments described herein are not limiting and one skilled in the art can readily appreciate that specific combinations of the modifications described herein can be tested without undue experimentation toward identifying nucleic acid molecules with improved RNAi activity.

All publications, patents and literature specifically mentioned herein are incorporated by reference in their entirety for all purposes.

It is understood that this invention is not limited to the particular methodology, protocols, materials, and reagents described, as these may vary. It is also to be understood that the terminology used herein is for the purpose of describing particular embodiments only, and is not intended to limit the scope of the present invention. It will be readily apparent to one skilled in the art that varying substitutions and modifications can be made to the description disclosed herein without departing from the scope and spirit of the description, and that those embodiments are within the scope of this description and the appended claims.

It must be noted that as used herein and in the appended claims, the singular forms "a", "an", and "the" include plural reference unless the context clearly dictates otherwise. As well, the terms "a" (or "an"), "one or more" and "at least one" can be used interchangeably herein. It is also to be noted that the terms "comprises," "comprising", "containing," "including", and "having" can be used interchangeably, and shall be read expansively and without limitation.

Recitation of ranges of values herein are merely intended to serve as a shorthand method of referring individually to each separate value falling within the range, unless otherwise indicated herein, and each separate value is incorporated into the specification as if it were individually recited herein. For Markush groups, those skilled in the art will recognize that this description includes the individual members, as well as subgroups of the members of the Markush group.

Without further elaboration, it is believed that one skilled in the art can, based on the above description, utilize the present invention to its fullest extent. The following specific embodiments are, therefore, to be construed as merely illustrative, and not limitative of the remainder of the disclosure in any way whatsoever.

All of the features disclosed in this specification may be combined in any combination. Each feature disclosed in this specification may be replaced by an alternative feature serving the same, equivalent, or similar purpose.

What is claimed is:

1. A nucleic acid molecule for inhibiting expression of p21 comprising a sense strand and an antisense strand, wherein the strands form a duplex region, and wherein the sense strand is CUCCCACAAUGCUGAAUAUmUmU (SEQ ID NOs:28) and the antisense strand is AUAUUCA-GCAUUGUGGGAGmUmU (SEQ ID NOs:56), wherein mU is 2'-methoxy-U.

2. The nucleic acid molecule of claim 1, wherein one or more of the nucleotides in the duplex region is modified or chemically-modified.

3. The nucleic acid molecule of claim 2, wherein the modified or chemically-modified nucleotides are 2'-deoxy nucleotides, 2'-O-alkyl substituted nucleotides, 2'-deoxy-2'-fluoro substituted nucleotides, phosphorothioate nucleotides, locked nucleotides, or any combination thereof.

4. The nucleic acid molecule of claim 2, wherein the antisense strand has deoxynucleotides in a plurality of positions, which plurality of positions are one of the following:

each of positions 4, 6 and 8, from the 5' end of the antisense strand;
each of positions 3, 5 and 7, from the 5' end of the antisense strand;
each of positions 1, 3, 5 and 7, from the 5' end of the antisense strand;
each of positions 3-8, from the 5' end of the antisense strand; or
each of positions 5-8, from the 5' end of the antisense strand.

5. The nucleic acid molecule of claim 4, wherein the molecule has one or more 2'-deoxy-2'-fluoro substituted nucleotides in the duplex region.

6. A pharmaceutical composition comprising the nucleic acid molecule of claim 1 and a pharmaceutically acceptable carrier.

7. The pharmaceutical composition of claim 6, wherein the carrier is a lipid molecule, nanoparticle or liposome.

8. A vector or cell comprising the nucleic acid molecule of claim 1.

9. A method for suppressing expression of p21 in a cell, comprising contacting the cell with a nucleic acid molecule of claim 1.

* * * * *